(12) United States Patent
Albrecht et al.

(10) Patent No.: US 9,868,690 B2
(45) Date of Patent: Jan. 16, 2018

(54) PRODRUGS OF MONOMETHYL FUMARATE (MMF)

(71) Applicant: RATIOPHARM GMBH, Ulm (DE)

(72) Inventors: Wolfgang Albrecht, Ulm (DE); Roland Selig, Ulm (DE); Sebastian Rabe, Neu-Ulm (DE); Richard Guserle, Kölz (DE); Annemarie Maier, Biberach (DE)

(73) Assignee: ratiopharm GmbH, Ulm (DE)

( * ) Notice: Subject to any disclaimer, the term of this patent is extended or adjusted under 35 U.S.C. 154(b) by 0 days.

(21) Appl. No.: 14/647,677

(22) PCT Filed: Dec. 20, 2013

(86) PCT No.: PCT/EP2013/077848
§ 371 (c)(1),
(2) Date: May 27, 2015

(87) PCT Pub. No.: WO2014/096425
PCT Pub. Date: Jun. 26, 2014

(65) Prior Publication Data
US 2015/0299103 A1    Oct. 22, 2015

(51) Int. Cl.
| | | |
|---|---|---|
| C07C 225/22 | (2006.01) |
| A61K 31/495 | (2006.01) |
| A61K 31/54 | (2006.01) |
| C07C 69/604 | (2006.01) |
| C07C 219/08 | (2006.01) |
| C07D 295/088 | (2006.01) |
| C07D 317/40 | (2006.01) |
| C07F 9/09 | (2006.01) |

(52) U.S. Cl.
CPC .......... *C07C 225/22* (2013.01); *A61K 31/495* (2013.01); *A61K 31/54* (2013.01); *C07C 69/604* (2013.01); *C07C 219/08* (2013.01); *C07D 295/088* (2013.01); *C07D 317/40* (2013.01); *C07F 9/091* (2013.01)

(58) Field of Classification Search
None
See application file for complete search history.

(56) References Cited

FOREIGN PATENT DOCUMENTS

WO    WO 2010022177 A2 *  2/2010   ............. C07C 69/60

* cited by examiner

*Primary Examiner* — Heidi Reese
(74) *Attorney, Agent, or Firm* — Milstein Zhang & Wu LLC

(57) ABSTRACT

The present invention relates to novel compounds for use as a medicament. In particular, the present invention relates to novel prodrugs of monomethyl fumarate (MMF) suitable as a medicament, preferably in the treatment and/or prevention of systemic diseases, autoimmune diseases, inflammatory diseases, for example multiple sclerosis and psoriasis.

12 Claims, 6 Drawing Sheets

PRODRUGS OF MONOMETHYL FUMARATE (MMF)

The present invention relates to novel compounds for use as a medicament. In particular, the present invention relates to novel prodrugs of monomethyl fumarate (MMF) suitable as a medicament, preferably in the treatment and/or prevention of systemic diseases, autoimmune diseases, inflammatory diseases, for example multiple sclerosis and psoriasis.

BACKGROUND OF THE INVENTION

Dimethyl fumarate (DMF) is an oral therapeutic agent which is reported to reduce the rejection often occurring in connection with organ transplantation (host versus graft reaction). Further, DMF is approved to be suitable as a medicament for the treatment or prevention of a variety of diseases. For example, DMF is proposed in the treatment of autoimmune diseases such as multiple sclerosis. Further, DMF is suggested to be a suitable active pharmaceutical agent in the treatment of psoriasis.

DMF is characterized by the following chemical Formula (1):

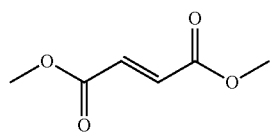

Formula (1)

When taken orally DMF is reported to be hydrolyzed for example by the acidic ambience of the stomach or by esterases in the intestine to monomethyl fumarate (MMF). MMF can be regarded as a metabolite of DMF and can be characterized by the following chemical Formula (2):

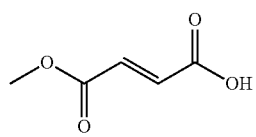

Formula (2)

The mechanisms of action of DMF or its metabolite MMF is reported to include inhibition of cytokine-induced nuclear translocation of the nuclear factor kappa B (NF-κB), apoptosis of stimulated T cells, and increased production of the $T_h2$ cytokines IL-4 and IL-5 in stimulated T cells, whereas generation of the $T_h1$ cytokine interferon gamma (IFN-γ) is supposed to remain unaffected. DMF is described to activate the transcription factor Nrf2 (nuclear factor erythroid 2-related factor 2), which binds to antioxidant response elements in the promoters of protective genes such as NADPH-quinone-oxidoreductase-1 (NQO1) and heme-oxygenase-1. Thus, this ultimately raises the levels of the important intracellular antioxidant glutathione (cf. Albrecht P. et al., Journal of Neuroinflammation 2012, 9:163).

Further, it is alleged that the treatment of animals or primary cultures of CNS cells with DMF or MMF resulted in increased nuclear levels of active Nrf2, with subsequent up-regulation of canonical antioxidant target genes. DMF or MMF treatment increased cellular redox potential, glutathione, ATP levels, and mitochondrial membrane potential in a concentration-dependent manner. Treating astrocytes or neurons with DMF or MMF also significantly improved cell viability after toxic oxidative challenge in a concentration-dependent manner. This effect on viability was lost in cells that had eliminated or reduced Nrf2. These data suggest that DMF and MMF are cytoprotective for neurons and astrocytes against oxidative stress-induced cellular injury and loss, potentially via up-regulation of an Nrf2-dependent antioxidant response. Thus, in summary, it is indicated that in vivo DMF and MMF show about the same efficacy, in particular on the transcription factor Nrf2.

As mentioned above, DMF is rather rapidly hydrolyzed to monomethyl fumarate (MMF) when taken orally for example by the acidic aqueous ambience of the stomach or by esterases in the (small) intestine. Thus, significant amounts of MMF are released within a short period of time. Such a rapid hydrolysis in principle was expected to provide a high level of MMF in the plasma within a short period of time.

However, it has been found that a high MMF plasma level might not be achievable. For example the organism might not be capable of transferring the whole amount of MMF to the sites of the body where the pharmacological action takes place.

Additionally it is reported that DMF has to be administered in quite high amounts and that the pharmaceutical active agent often shows undesirable side effects, such as flush, and especially symptoms related to the gastrointestinal tract such irritation of the stomach and diarrhoea.

Consequently, there is a need for new medicaments, preferably in the treatment and/or prevention of systemic diseases, autoimmune diseases, inflammatory diseases, for example multiple sclerosis and psoriasis. The medicaments should be capable of being applied in appropriate doses and should not cause significant undesired side effects.

Hence, it was an object of the present invention to overcome the drawbacks of the above-mentioned marketed drug substance DMF.

It was an object to develop a compound to be used as a medicament for the above-mentioned diseases wherein said compound shows advantageous pharmacokinetic properties.

Moreover, compounds should be provided which are hydrolysed within the human body to MMF more slowly than DMF (or alternatively under respective in-vitro conditions).

Further, the compound should preferably cause few undesirable side effects.

Additionally, it was an object of the present invention to provide compounds which can be used in the treatment of the early phase of an autoimmune disease, in particular of multiple sclerosis, such that the progress of the disease can be delayed.

SUMMARY OF THE INVENTION

According to the present invention, the above objectives are achieved by the specific compounds described herein by Formulae (I) to (VI) or mixtures thereof for use as a medicament. Said compounds, which can preferably be regarded as prodrugs of MMF, can be used as a medicament for the treatment and/or prevention of systemic diseases, autoimmune diseases, inflammatory diseases, for example multiple sclerosis and psoriasis.

Generally, a prodrug can be regarded as a substance that is administered to a subject (preferably human) in a pharmacologically inactive or pharmacologically less than fully active form, and is subsequently converted in the body of the subject to an active drug, preferably through metabolic processes occurring in the body of the subject. In other words, a prodrug usually serves as a type of 'precursor' to the intended drug.

Thus, the subject of the present invention is a compound according to any one of the following Formulae (I) to (VI) or mixtures thereof for use as a medicament:

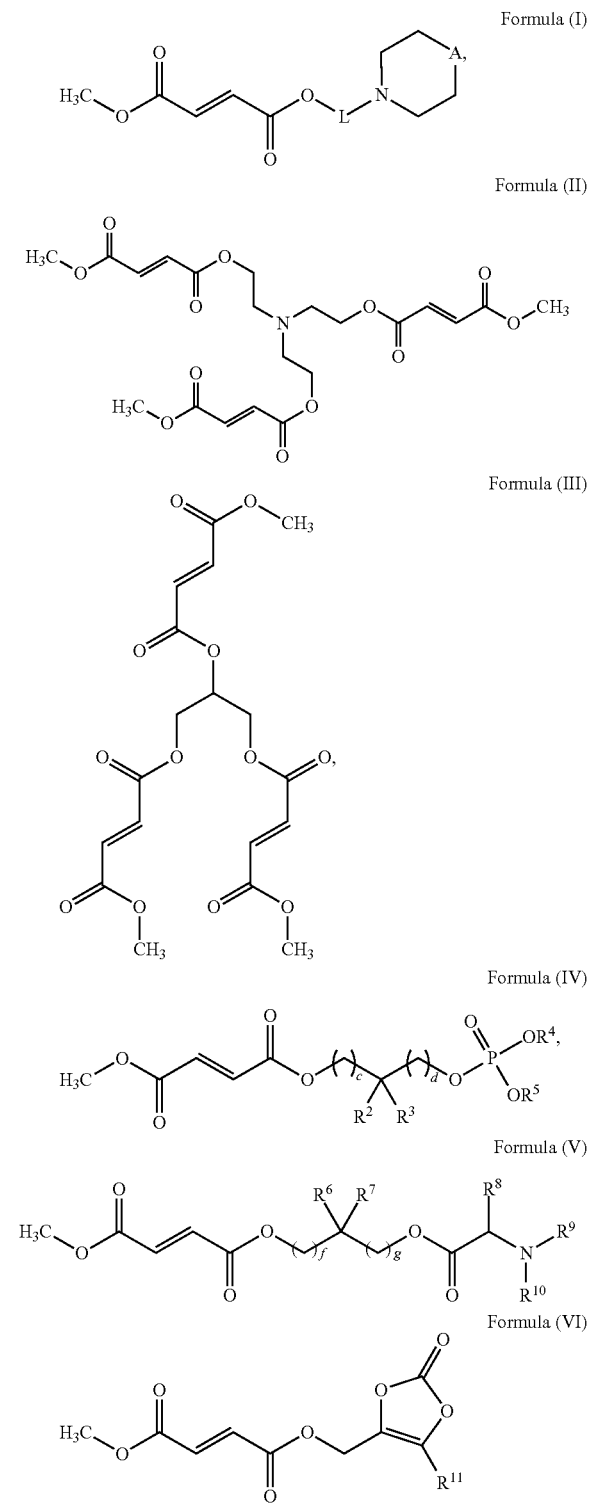

wherein
L is an alkanediyl group with 1 to 6 carbon atoms
A is SO, $SO_2$ or $NR^1$, and
$R^1$, $R^2$, $R^3$, $R^4$, $R^5$, $R^6$, $R^7$, $R^8$, $R^9$, $R^{10}$ and $R^{11}$ are each independently an organic residue, and
c and d are independently an integer from 0 to 3,
f and g are independently an integer from 0 to 3 with the proviso that both f and g cannot be 0.

It was found that the compounds of the present invention show superior pharmaceutical and/or pharmacokinetic properties. In particular, the compounds show an advantageous hydrolysis rate such that the appropriate dose of the compound can be applied to the patient.

The present invention further relates to a pharmaceutical composition comprising one or more of the inventive compounds.

Another subject of the present invention is the process for producing a compound according to the present invention by reacting an activated form of monomethyl fumarate with a substance comprising at least one hydroxy group.

DETAILED DESCRIPTION OF THE INVENTION

Figure 1:
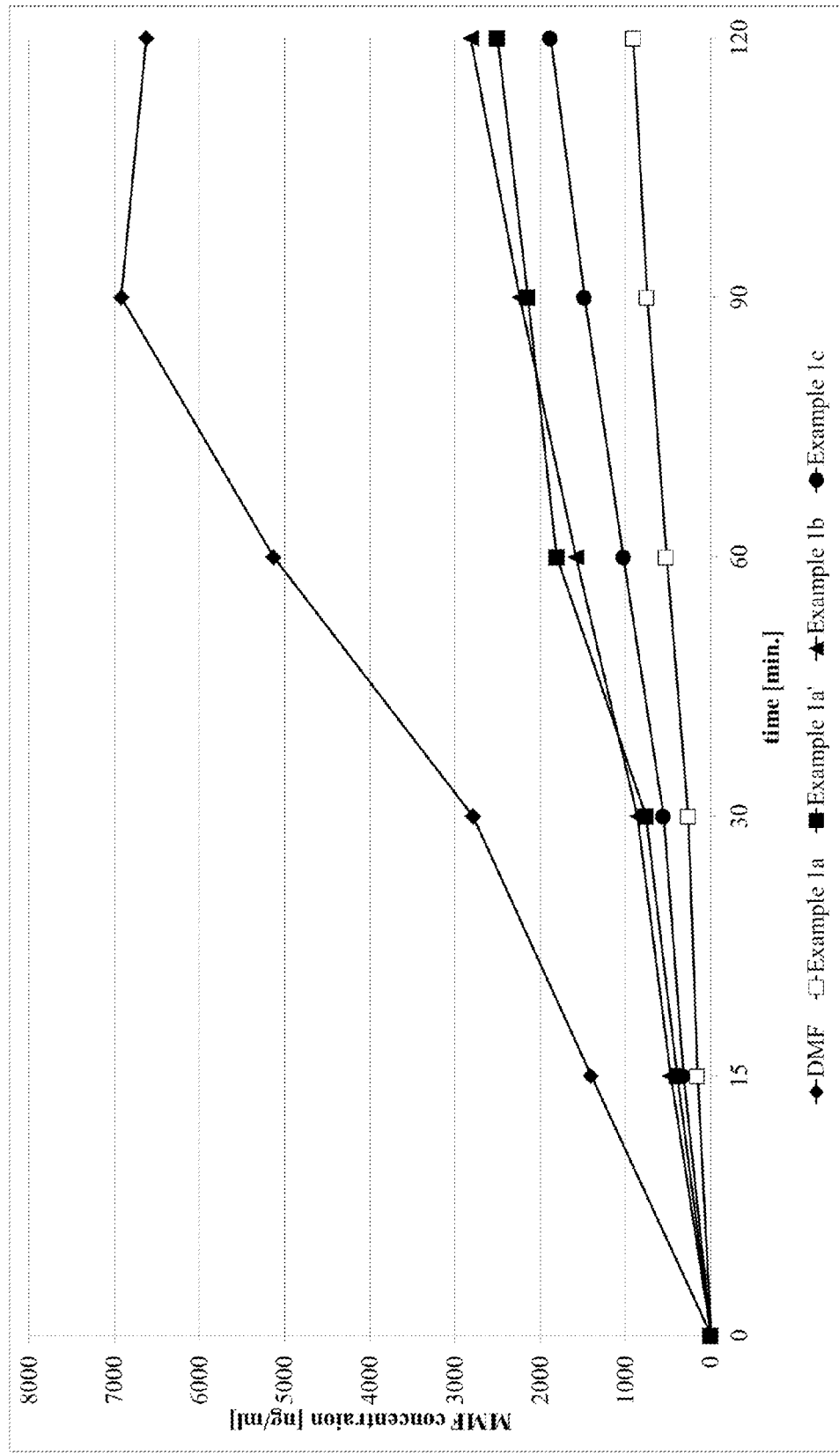
FIG. 1 depicts data of Examples 1a, 1a', 1b and 1c, showing significantly slower hydrolysis to MMF than DMF.

In the context of this invention, the compound for use as a medicament refers to the above Formulae (I) to (VI). Further, these compounds may refer to pharmaceutically acceptable salts, hydrates, solvates, polymorphs, stereoisomers and mixtures thereof.

In a particularly preferred embodiment of the present invention a single compound according to any one of Formulae (I) to (VI) can be used as a medicament. In an alternative embodiment of the present invention a combination of any of the compounds according to Formulae (I) to (VI) can be used as a medicament.

The same applies to the pharmaceutical composition comprising the compound(s) which are represented by Formulae (I) to (VI).

In a compound according to Formula (I) L is an alkanediyl group with 1 to 6 carbon atoms or alternatively 2, 3 or 4 carbon atoms.

Alkanediyl groups with 1 to 6 carbon atoms comprise linear and branched alkanediyl groups with 1 to 6 carbon atoms. Examples for alkanediyl groups with 1 to 6 carbon atoms are —$CH_2$—, —$(CH_2)_2$—, —$CH(CH_3)$—, —$(CH_2)_3$—, —$CH_2CH(CH_3)$—, —$CH(CH_3)CH_2$—, —$CH(C_2H_5)$—, —$C(CH_3)_2$—, —$(CH_2)_4$—, —$(CH_2)_2CH(CH_3)$—, —$CH_2CH(CH_3)CH_2$—, —$CH(CH_3)(CH_2)_2$—, —$CH(C_2H_5)CH_2$—, —$CH_2CH(C_2H_5)$—, —$C(CH_3)_2CH_2$—, —$CH_2C(CH_3)_2$—, —$CH(CH_3)CH(CH_3)$, —$CH(C_3H_7)$—, —$(CH_2)_5$—, —$(CH_2)_3CH(CH_3)$, —$(CH_2)_2CH(CH_3)CH_2$—, —$CH_2CHCH_3(CH_2)_2$—, —$CH_2C(CH_3)_2CH_2$—, —$(CH_2)_2C(CH_3)_2$—, —$(CH_2)_6$—, —$(CH_2)_4CH(CH_3)$—, —(CH$_2$)$_3$CH(CH$_3$)CH$_2$—, —CH$_2$CHCH$_3$(CH$_2$)$_3$—, —(CH$_2$)$_3$C(CH$_3$)$_2$— and —(CH$_2$)$_2$C(CH$_3$)$_2$CH$_2$—.

In a preferred embodiment L is a linear alkanediyl group with 1 to 6 carbons atoms, preferably with 2, 3 or 4 carbon atoms, more preferably with 2 or 4 carbon atoms, in particular with 2 carbons atoms.

In a particularly preferred embodiment in Formula (I) L can be —(CH$_2$)$_2$— and A can be SO$_2$ and thus the corresponding compound can be represented by following Formula (Ia)

Formula (Ia)

In a particularly preferred embodiment in Formula (I) L can be —(CH$_2$)$_2$— and A can be SO and thus the corresponding compound can be represented by following Formula (Ia')

Formula (Ia')

In a preferred embodiment of the invention in Formula (I) R$^1$ can be alkyl with 1 to 6 carbon atoms or cyclic alkyl with 3 to 6 carbon atoms.

Alkyl with 1 to 6 carbon atoms can for example include methyl, ethyl, propyl, butyl, isobutyl, tert.butyl, pentyl, sec.-pentyl, and hexyl.

Cyclic alkyl with 3 to 6 carbon atoms can for example include cyclopropyl, cyclobutyl, cyclopentyl and cyclohexyl.

It is preferred that in Formula (I) R$^1$ can be alkyl with 1 to 4 carbon atoms or cycloalkyl with 3, 5 or 6 carbon atoms, more preferably alkyl with 1 to 3 carbon atoms.

In a particularly preferred embodiment in Formula (I) L can be —(CH$_2$)$_2$— and A can be NR$^1$ with R$_1$ being methyl and thus the corresponding compound can be represented by following Formula (Ib)

Formula (Ib)

In an alternative particularly preferred embodiment in Formula (I) L can be —(CH$_2$)$_2$— and A can be NR$^1$ with R$_1$ being isopropyl and thus the corresponding compound can be represented by following Formula (Ic)

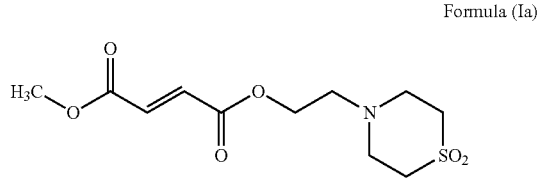 [SMILES: COC(=O)/C=C/C(=O)OCCN1CCS(=O)(=O)CC1]

Formula (Ic)

The compound according to Formula (I) can preferably comprise the pharmaceutically acceptable acid addition salts of the inventive compound. The acids which are used to prepare the pharmaceutically acceptable acid addition salts are preferably those which form non-toxic acid addition salts, i.e. salts containing pharmacologically acceptable anions, such as chloride, bromide, iodide, nitrate, sulfate, bisulfate, phosphate, acid phosphate, acetate, lactate, citrate, (D,L)- and L-tartrate, (D,L)- and L-malate, bitartrate, succinate, maleate, fumarate, gluconate, saccharate and benzoate. A preferred salt is the corresponding hydrochloride or dihydrochloride of a compound according to Formula (I).

A compound according to Formula (I) can preferably be synthesized via the following route:

Formula (I)

Preferably, in step a, MMF and the oxidized thiomorpholin-4-yl alkyl alcohol or 4-alkyl piperazin-1-yl alkyl alcohol can be submitted to an esterification in an organic solvent in the presence of a coupling agent. A coupling agent is preferably a substance generally facilitating the formation of an ester or an amide. The coupling agent reacts with a carboxy group by forming a reactive intermediate which is subsequently further reacted with an alcohol or an amine to form the final product, i.e. an ester or an amide. Coupling agents are reported to be used in case that one or both of the educts further bear a group being labile in acidic or alkaline milieu, since the reaction is carried out under neutral conditions. Suitable coupling agents can be for example DCC (N,N'-dicyclohexylcarbodiimide), DIC (N,N'-diisopropylcarbodiimide), EDC (N-ethyl-N'-(3-methylaminopropyl) carbodiimide hydrochloride), CDI (carbonyldiimidazole), preferably EDC in combination with DMAP (4-(dimethylamino)pyridine).

A suitable organic solvent can for example be dichloromethane, chloroform, dioxane, tetrahydrofuran, acetonitrile and dimethyl formamide.

Alternatively, MMF can be preferably reacted with thionyl chloride or oxalyl chloride, preferably oxalyl chloride, to form the corresponding acid chloride. Subsequently, the corresponding acid chloride can be submitted to a reaction with oxidized thiomorpholin-4-yl alkyl alcohol or 4-alkyl piperazin-1-yl alkyl alcohol preferably in an organic solvent, such as dioxane, tetrahydrofuran, chloroform or dichloromethane. Further, the reaction of the acid chloride with oxidized thiomorpholin-4-yl alkyl alcohol or 4-alkyl piperazin-1-yl alkyl alcohol is preferably carried out in the presence of an auxiliary alkaline compound. Suitable alkaline compounds are for example pyridine and amines, such triethylamine, and diisopropylethylamine, preferably triethylamine.

A further compound according to the present invention is represented by Formula (II)

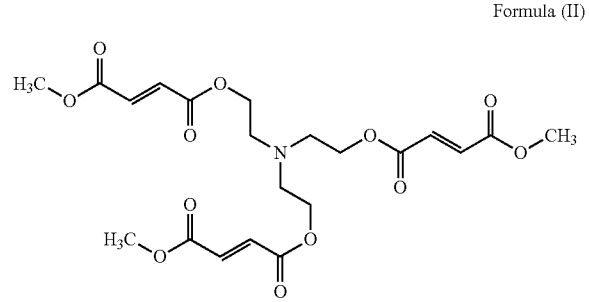

Formula (II)

A compound according to Formula (II) can preferably be synthesized via the following route:

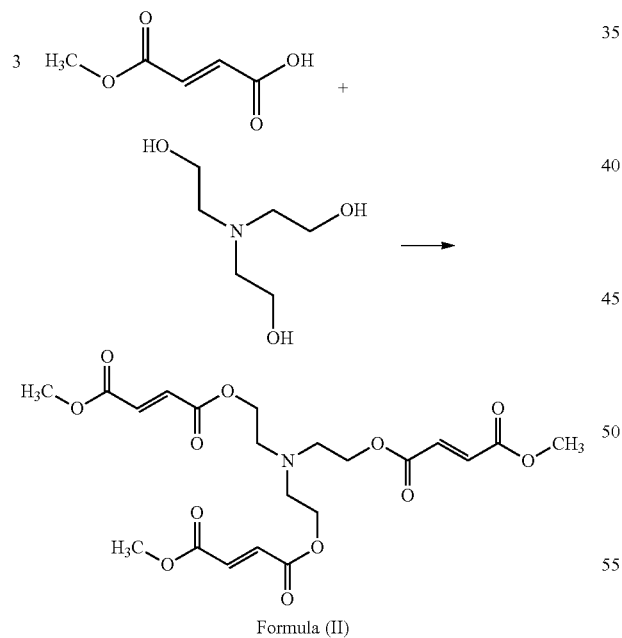

Formula (II)

The compound according to Formula (II) can preferably be synthesized in substantially the same way as described above with regard to the synthesis of Formula (I). Thus, a compound according to Formula (II) can be obtained by an esterification of an equivalent amount of MMF with triethanol amine (tris-(2-hydroxyethyl)amine) in the presence of a coupling agent. Alternatively, MMF can be first converted to the corresponding acid chloride before being conducted to a reaction with the triethanol amine (tris-(2-hydroxyethyl) amine). Generally the same conditions as mentioned above for the synthesis of Formula (I) can preferably be applied.

A compound according to Formula (II) can preferably be present in form of an acid addition salt. Examples for suitable salts comprise the ones mentioned above with regard to Formula (I). In a preferred embodiment a compound according to Formula (II) is present in form of its hydrochloride.

A further compound according to the present invention is represented by Formula (III)

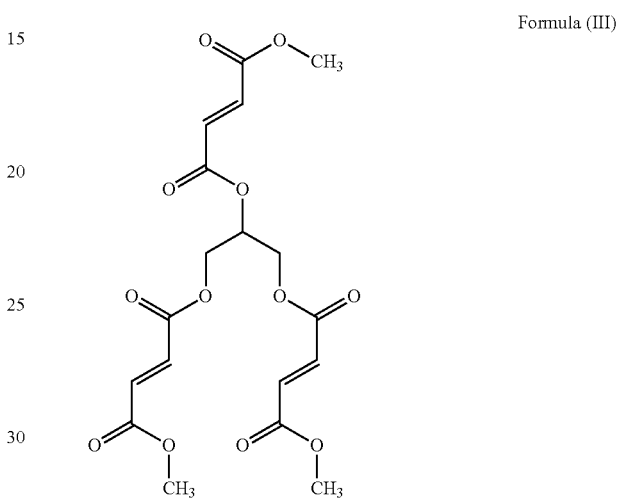

Formula (III)

A compound according to Formula (III) can preferably be synthesized via the following route:

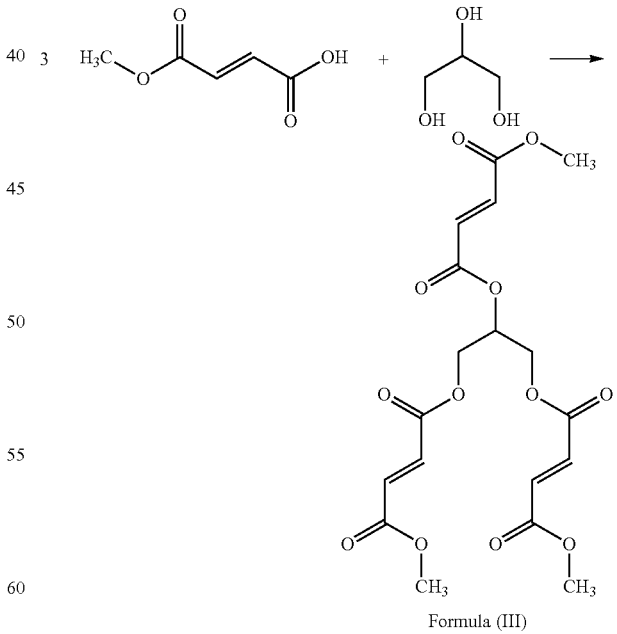

Formula (III)

The compound according to Formula (III) can preferably be synthesized in substantially the same way as described above with regard to the synthesis of Formula (I). Thus, a compound according to Formula (III) can be obtained by an esterification of an equivalent amount of MMF with glycerol (1,2,3-trihydroxpropane) in the presence of a coupling agent. Alternatively, MMF can be first converted to the corresponding acid chloride before being conducted to a reaction with the glycerol (1,2,3-trihydroxpropane). Generally the same conditions as mentioned above for the synthesis of Formula (I) can preferably be applied.

In a preferred embodiment of the invention $R^2$ and $R^3$ in Formula (IV) are independently hydrogen, alkyl with 1 to 6 carbon atoms or cyclic alkyl with 3 to 6 carbon atoms. In a more preferred embodiment $R^2$ and $R^3$ can be independently hydrogen, methyl and ethyl, more preferably hydrogen or methyl. It is particularly preferred that $R^2$ and $R^3$ are both hydrogen or that one of $R^2$ and $R^3$ is methyl while the other one is hydrogen. Further, it is preferred that the main chain linking the MMF with the phosphate does not have more than 3 carbon atoms. It is further preferred that c and d can be independently 0 or 1; more preferably c and d are both 0.

It is preferred that $R^4$ and $R^5$ in Formula (IV) can be independently hydrogen or alkyl with 1 to 6 carbon atoms, more preferably alkyl with 1 to 5 carbon atoms, even more preferably alkyl with 1 to 4 carbon atoms, in particular tert.butyl. It is further preferred that $R^4$ and $R^5$ are identical.

In a particularly preferred embodiment in Formula (IV) c and d can be 0, $R^2$ and $R^3$ can be hydrogen and ethyl and $R^4$ and $R^5$ can be tert.butyl and thus the corresponding compound can be represented by following Formula (IVa)

Formula (IVa)

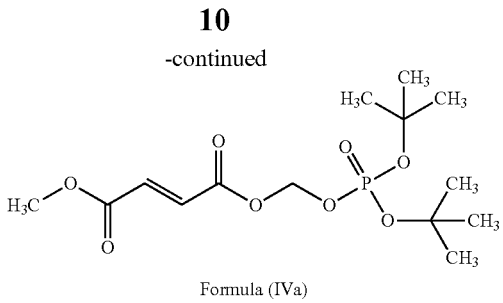

Formula (IVa)

In step a', MMF can preferably be reacted with thionyl chloride or oxalyl chloride, preferably oxalyl chloride, to form the corresponding acid chloride. The formation of the acid chloride is preferably conducted under the conditions as mentioned above.

This acid chloride is submitted to a reaction with $OCR^2R^3$ (in the present case $R^2=R^3=$hydrogen) in step b'.

In step c', the product resulting from step b' can be reacted with a phosphate diester (in the present case $R^4=R^5=$tert.butyl) to a compound according to Formula (IVa).

Alternatively, a compound according to Formula (IVa) can preferably be synthesized via the following route

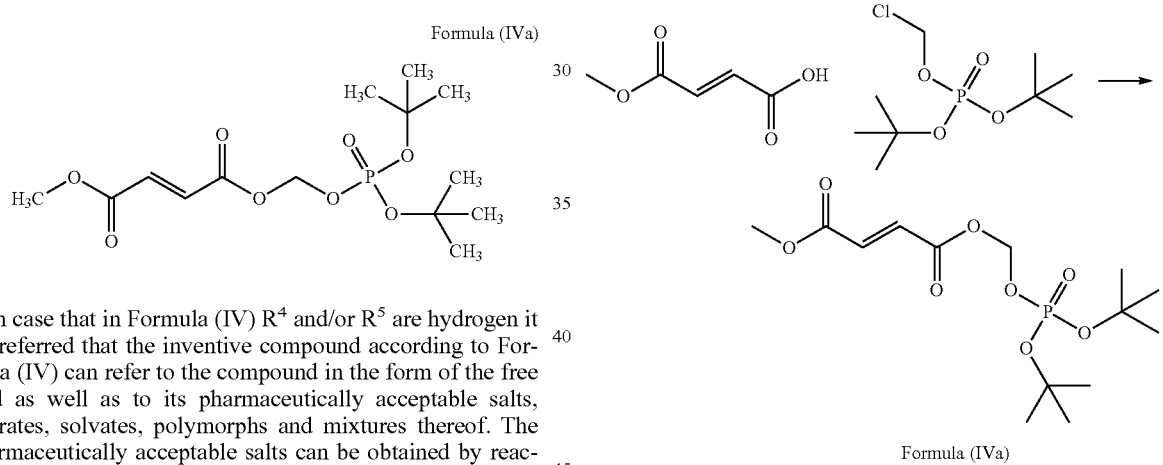

Formula (IVa)

In case that in Formula (IV) $R^4$ and/or $R^5$ are hydrogen it is preferred that the inventive compound according to Formula (IV) can refer to the compound in the form of the free acid as well as to its pharmaceutically acceptable salts, hydrates, solvates, polymorphs and mixtures thereof. The pharmaceutically acceptable salts can be obtained by reaction, preferably with an inorganic base. Thereby, one or both of the phosphate hydrogen atom(s) of the compound can be replaced by a metal atom, for example sodium. Alternatively, the salt can be formed together with a dialkylamine or a trialkylamine, preferably a trialkylamine. Examples of trialkylamines comprise diethylmethylamine, triethylamine, diisopropylethylamine, diethylisopropylamine. Triethylamine is particularly preferred.

A compound according to Formula (IVa) can preferably be synthesized via the following route:

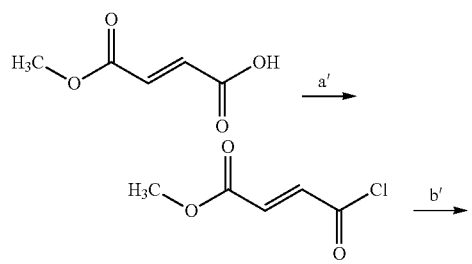

MMF and di-tert.butyl chlormethyl phosphate were preferably reacted in a solvent such as dimethylformamide to the compound according to Formula (Iva). The reaction preferably is conducted at a temperature form 0° C. to 40° C., more preferably at room temperature (23° C.). Additionally, the reaction is preferably conducted in the presence of an alkaline compound, more preferably an inorganic alkaline compound, even more preferably an alkali or an earth alkali carbonate, in particular caesium carbonate.

In a preferred embodiment of the invention $R^6$, $R^7$, $R^9$ and $R^{10}$ in Formula (V) can independently be hydrogen, alkyl with 1 to 6 carbon atoms or cyclic alkyl with 3 to 6 carbon atoms, and $R^3$ can be hydrogen, cyclic alkyl with 3 to 6 carbon atoms or alkyl with 1 to 6 carbon atoms wherein the alkyl with 1 to 6 carbon atoms can be substituted, and wherein one of $R^9$ and $R^{10}$ together with $R^8$ optionally belong to a 5 or 6-membered heteroaliphatic ring.

Alkyl and cyclic alkyl correspond to the definition described above.

In case that $R^8$ is a substituted alkyl with 1 to 6 carbon atoms the substituents can preferably be selected from one or more of the following substituents: halogen, nitro, nitrile, urea, phenyl, aldehyde, sulfate, amino, NH—C(NH)NH$_2$, carboxamide, carboxylic acid, hydroxy, imidazole, indole, mercapto, methylthio, phenyl, hydroxyphenyl. Especially preferred are one or more of the following substituents: amino, NH—C(NH)NH$_2$, carboxamide, carboxylic acid, hydroxy, imidazole, indole, mercapto, methylthio, phenyl, hydroxyphenyl.

In a particularly preferred embodiment $R^8$ can be —CH$_2$—C$_6$H$_5$.

In a preferred embodiment of the invention one of $R^9$ and $R^{10}$ in Formula (V) is hydrogen and the other of $R^9$ and $R^{10}$ and further $R^8$ are alkyl wherein $R^9$ and $R^8$ or $R^{10}$ and $R^8$ optionally belong to a 5 or 6-membered heteroaliphatic ring.

In a further preferred embodiment of the invention $R^9$ and $R^{10}$ both are hydrogen and $R^8$ can preferably be hydrogen, alkyl with 1 to 3 carbon atoms or alkyl with 1 to 4 carbon atoms substituted with one or more substituents as described above. It is particularly preferred that $R^8$ can be —CH$_3$.

The compound according to Formula (V) can represent a monomethyl fumarate which is coupled via a linking group to an amino acid. The linking group can be represented by
—(CH$_2$)$_f$—CR$^6$R$^7$—(CH$_2$)$_g$—.

In a further preferred embodiment $R^6$ and $R^7$ can preferably be independently hydrogen or alkyl with 1 or 2 carbon atoms. It is preferred that $R^6$ and $R^7$ are both hydrogen or alternatively that one of $R^6$ and $R^7$ is hydrogen and the other of $R^6$ and $R^7$ is methyl. Further, it is preferred that the main chain of the linking group connecting the monomethyl fumarate to the amino acid does not have more than four carbon atoms.

In a preferred embodiment one of f and g can preferably be 0. Preferably g is 0.

In a particularly preferred embodiment in Formula (V) the linking group can be ethyl and $R^8$ can be isopropyl and $R^9$ and $R^{10}$ can be hydrogen and thus the corresponding compound can be represented by following Formula (Va)

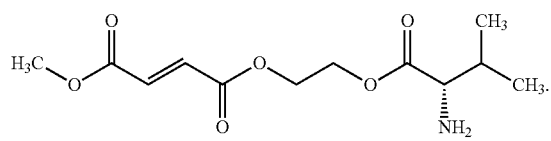

Formula (Va)

A compound according to Formula (Va) can preferably be present in form of an acid addition salt. Examples for suitable salts comprise the ones mentioned above with regard to Formula (I). In a preferred embodiment a compound according to Formula (Va) is present in form of its hydrochloride.

A compound according to Formula (Va) can preferably be synthesized via the following route:

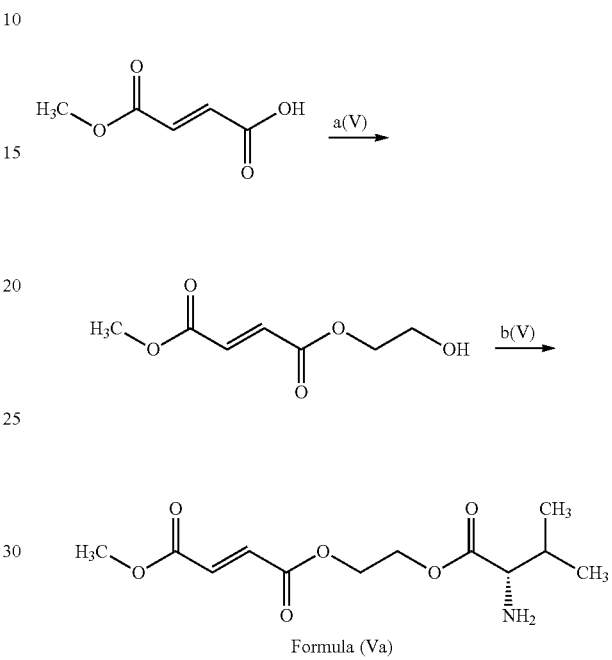

Formula (Va)

In step a(V), MMF can preferably be submitted to a reaction with ethylene glycol. In step b(V) the product resulting from step a(V) can be reacted with the hydroxy group of the carboxy group of an amino acid. In a preferred embodiment, any further hydroxy or amino group of the amino acid can preferably be protected, more preferably Boc-protected, before reaction step b(V) and deprotected after reaction step b(V).

Alternatively, a compound according to Formula (Va) can preferably be synthesized via the following alternative route:

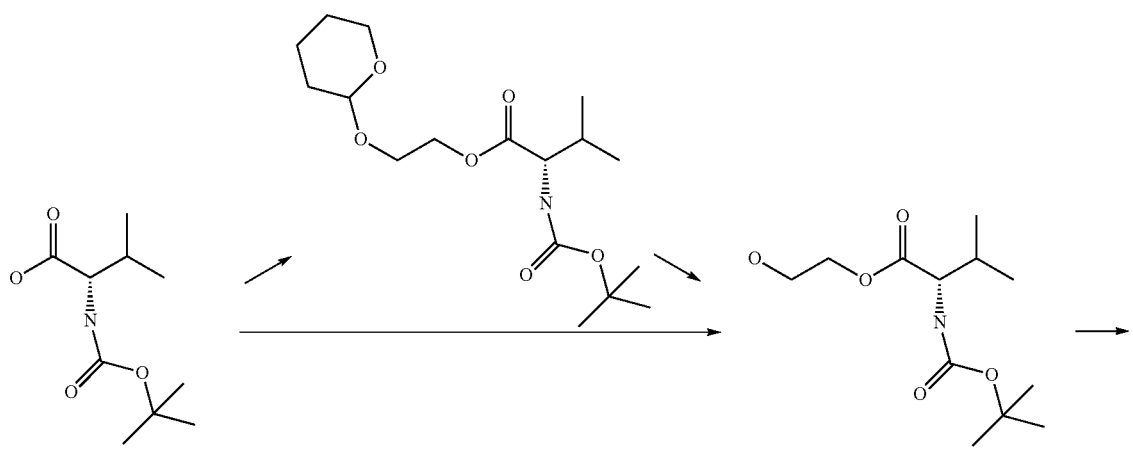

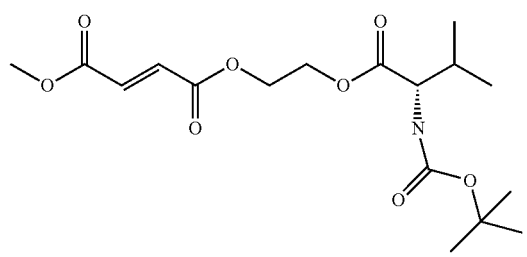 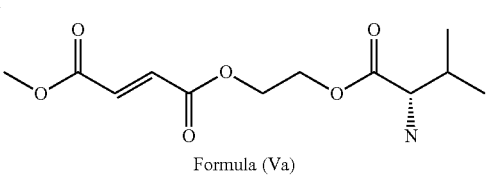

Formula (Va)

An amino acid which amine group is Boc-protected is coupled with ethylene glycol or a protected ethylene glycol, such THP-ethylene glycol, in the presence of a coupling agent and solvent as mentioned above. Further, if necessary the protection group of the ethylene glycol is removed.

In a second step the product resulting from first step is coupled with to MMF. This reaction is preferably carried out in the presence of a coupling agent and solvent as mentioned above.

Further, the Boc-protection group of the amine is removed and the product according to Formula (Va) is obtained.

In an alternative, particularly preferred embodiment the linking group in Formula (V) can be ethyl and $R^8$ can be $—CH_2—C_6H_5$ and $R^9$ and $R^{10}$ can be hydrogen and thus the corresponding compound can be represented by following Formula (Vb)

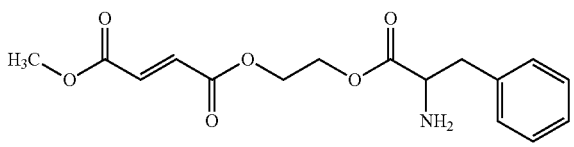

Formula (Vb)

A compound according to Formula (Vb) can preferably be present in form of an acid addition salt. Examples for suitable salts comprise the ones mentioned above with regard to Formula (I). In a preferred embodiment a compound according to Formula (Vb) is present in form of its hydrochloride.

A compound according to Formula (Vb) can preferably be synthesized similar to a compound according to Formula (Va), wherein in step b(V) the corresponding amino acid or Boc-protected amino acid is used.

A preferred embodiment of the invention is a component which can be represented by the following Formula (Vc):

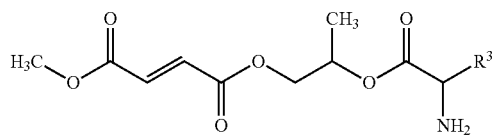

Formula (Vc)

A compound according to Formula (Vc) can preferably be synthesized similar to a compound according to Formula (Va), wherein in step a(V) proyleneglycol and in step b(V) the corresponding amino acid or Boc-protected amino acid is used.

A compound according to Formula (Vc) can preferably be present in form of an acid addition salt. Examples for suitable salts comprise the ones mentioned above with regard to Formula (I). In a preferred embodiment a compound according to Formula (Vc) is present in form of its hydrochloride.

The above compounds according to Formula V show excellent pharmacokinetic properties. The MMF is formed by hydrolysis. A further by-product is an amino acid, which can be further absorbed by the patient's organism or alternatively said amino acid can be easily excreted. In either case, said substance is not expected to harm the patient's organism.

In a preferred embodiment of the invention in Formula (VI) $R^{11}$ can preferably be hydrogen, alkyl with 1 to 6 carbon atoms or cyclic alkyl with 3 to 6 carbon atoms, alkenyl with 2 to 6 carbon atoms, halogen, cyano, hydroxy, amino, carboxy, mercapto, 5 or 6-membered aryl or hetero aryl optionally substituted with one or more of the following substituents: methyl, tert.butyl, hydroxy, methoxy, halogen, nitro, nitrile, amine, carboxamide. It is more preferred that $R^{11}$ can be hydrogen, alkyl with 1 or 2 carbon atoms, halogen, cyano, amino or hydroxy. In particular, it is preferred that $R^{11}$ is hydrogen, hydroxy or methyl, especially methyl.

A compound according to Formula (VI) can preferably be synthesized via the following route:

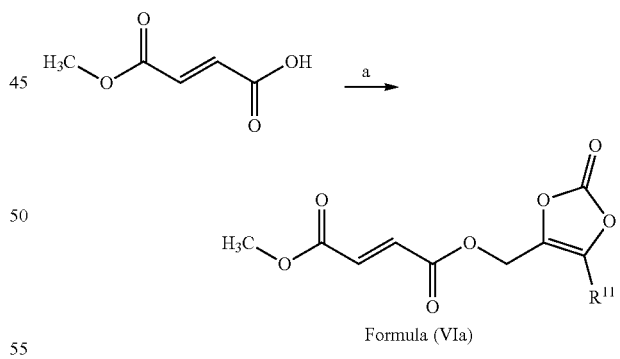

Formula (VIa)

In step a, MMF can be reacted with the hydroxy group of the 4-hydroxymethyl-1,3 dioxol-2-one substituted by $R^{11}$ in 5-position in the presence of a coupling agent and the corresponding conditions as described above.

In a preferred embodiment, MMF can be transformed to the corresponding acid chloride before reacting with the hydroxy group of the above 4-hydroxymethyl dioxol-2-one derivate.

In a particularly preferred embodiment $R^{11}$ is methyl and the corresponding compound is represented by the following Formula (VIa).

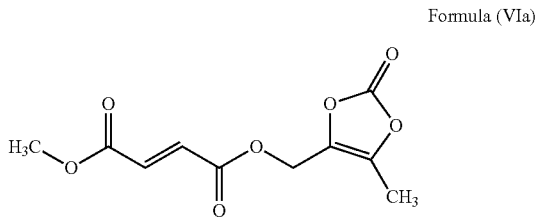 [SMILES: COC(=O)/C=C/C(=O)OCc1oc(=O)oc1C]

Formula (VIa)

The compound according to Formula (VIa) can be synthesized by reacting 4,5-dimethyl-1,3-dioxol-2-one with NBS to 4-(bromomethyl)-5-methyl-1,3-dioxol-2-on. 4-(Bromomethyl)-5-methyl-1,3-dioxol-2-on is further submitted to a reaction with MMF under alkaline conditions to form a compound according to Formula (VIa).

In a preferred embodiment the inventive compounds are for use in the treatment and/or prevention of systemic diseases, autoimmune diseases or inflammatory diseases.

Systemic diseases do not just affect single organs. Instead these diseases are known to affect a number of organs and tissues or even the body as a whole.

People having an autoimmune disease usually suffer from their immune system mistakenly attacking their own cells of their organism and thus incorrectly responding to substances normally present in the body.

An inflammation can be defined as the response of the body to the occurrence of harmful stimuli which can result in pain, heat, redness, swelling and loss of function of the affected organ.

It is possible that some of the above-mentioned diseases cannot be allocated in one single group of the above-mentioned groups, since they show the symptoms of more than one of them.

In a further preferred embodiment the inventive compound is for use in the treatment of multiple sclerosis and psoriasis, preferably multiple sclerosis. The compounds of the present invention can e.g. be used in the treatment of the following types of multiple sclerosis: relapsing-remitting, primary-progressive, secondary-progressive, and progressive-relapsing. In a preferred embodiment the compounds of the present invention are used in the treatment of relapsing-remitting multiple sclerosis.

Further, the present invention also provides a pharmaceutical composition comprising the compound according to the present invention, i.e. a pharmaceutical composition comprising a compound according to one of Formulae (I) to (VI) or a mixture thereof and optionally pharmaceutical excipients.

In a preferred embodiment the pharmaceutical composition comprises
(i) 0.01 to 10 mmol, more preferably 0.05 to 5 mmol, still more preferably 0.25 to 3.5 mmol and particularly preferably 0.5 to 2.5 mmol of a compound according to the present invention;
(ii) pharmaceutical excipient(s).

In a further preferred embodiment the present composition can comprise one or more further excipients, preferably pharmaceutical excipients as described in the European Pharmacopoeia (Ph.Eur.) and/or in the US Pharmacopoeia (USP).

Examples of pharmaceutical excipients are carriers, binders, fillers, disintegrants, wicking agents, glidants and/or lubricants.

In an embodiment the excipients are chosen such that the resulting formulation is a gastric juice-resistant formulation. In said embodiment the formulation of the present invention does not show significant drug release under acidic conditions. In particular, the in-vitro drug release after 2 hours is less than 10%, preferably 0 to 9.9%, more preferably 0 to 5%, still more preferably 0.001 to 3%, measured according to USP, Apparatus II, paddle, 0.1N HCl, 37° C., 50 rpm.

In an alternative embodiment the excipients are chosen such that the resulting formulation is an immediate release formulation. Preferably, the immediate release formulation does not comprise a gastric-juice coating. In said embodiment the in-vitro drug release after 15 min can be 60 to 100%, preferably 70 to 99.9%, more preferably 75 to 99.9, measured according to USP, Apparatus II, paddle, 0.1N HCl, 37° C., 50 rpm.

In an alternative embodiment the excipients are chosen such that the resulting formulation is a sustained release formulation. In said embodiment the in-vitro drug release after 2 hours can be 0 to 50%, after 4 hours 10 to 70%, after 6 hours 20 to 90%, wherein the first to hours are measured according to USP, Apparatus II, paddle, 0.1N HCl, 37° C., 50 rpm and the following hours are measured according to USP, Apparatus II, paddle, pH 6.8, 37° C., 50 rpm.

The pharmaceutical composition can be in a form suitable for oral administration, preferably in the form of a tablet or capsule, in particular in form of a tablet.

It is further preferred that the tablet is coated with a film coating. Alternatively, the capsule can also be coated.

In the present invention, the following three types of film coatings are possible:
film coating without affecting the release of the active ingredient,
gastric juice-resistant film coatings,
retard film coatings.

Generally, film coatings can be prepared by using film-forming agents such as waxes, cellulose derivatives, poly(meth)acrylate, polyvinylpyrrolidone, polyvinyl acetate phthalate, and/or shellac or natural rubbers such as carrageenan.

It is preferred that the present tablet is coated with a gastric juice-resistant film coating. Alternatively, a capsule comprising a gastric juice-resistant film coating can be used.

The gastric juice-resistant film coating preferably is a film coating being stable in the pH range of about 0.7 to 3.0, which is supposed to be the pH-value of human gastric juice found in the stomach. However, in a an environment with a pH value of 5 to 9, which is supposed to be present in the (small) intestine of the human body, the gastric juice-resistant film coating preferably dissolves and the drug can be released.

The gastric juice-resistant film coating (often also referred to as enteric coating) can comprise film-forming agents being for example fats, fatty acids, waxes, alginates, shellac, polyvinyl acetate phthalate, cellulose derivatives such as carboxy methyl ethyl cellulose, cellulose acetate succinate, cellulose acetate phthalate, hydroxypropyl methyl cellulose phthalate, hydroxypropyl methyl cellulose acetate succinate, cellulose acetate trimellitat, and meth(acrylic)acid copolymers such as methyl acrylate-methacrylic acid copolymers, methyl methacrylate-methacrylic acid copolymers, Eudragits (for example Eudragit® L30D, Eudragit® L, Eudragit® S).

The coating is preferably free of active ingredient. It is further preferred that the thickness of the coating is usually 10 μm to 2 mm, preferably from 50 to 500 μm.

The preferred coating may comprise a film-forming agent and one or more of the following: lubricant, surfactant, glidant, pigment and water.

The preferred coating according to an embodiment of the present invention can comprise, along with the film-forming agent, e.g. stearic acid as lubricant for plasticizing and dissolving the polymer, sodium lauryl sulfate as a surfactant for wetting and dispersing, talc as glidant, iron oxide yellow and/or titanium oxide as pigment(s) and optionally purified water.

In a preferred embodiment the pharmaceutical composition can be administered one to three times a day, preferably two or three times a day, more preferably two times a day.

The invention is illustrated by the following examples.

EXAMPLES

Example 1a

Synthesis of (E)-But-2-enedioic acid 2-(1,1-dioxo-1-lambda*6*-thiomorpholin-4-yl)-ethyl ester methyl ester

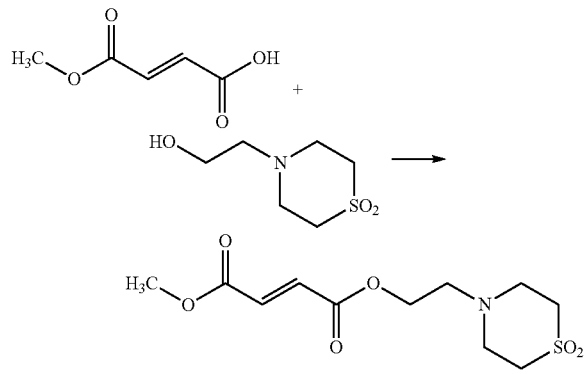

To a stirred suspension of monomethyl fumarate (1.5 g; 11.5 mmol) in dry dichloromethane (30 mL) were added successively N-ethyl-N'-(3-methylaminopropyl)carbodiimide hydrochloride (2.4 g; 12.7 mmol), 4-(2-hydroxyethyl)-1,1-dioxo-1-lambda*6*-thiomorpholine (2.3 g; 11.3 mmol) and DMAP (140 mg; 1.2 mmol) at 0° C. The suspension was allowed to warm to room temperature (23° C.) and stirring was continued overnight (for 14 hours). The mixture was diluted with additional dichloromethane (50 mL), washed with water (2×70 mL) and dried with sodium sulfate. After the removal of the solvent the resulting crude product was purified via silicagel chromatography (eluent: ethyl acetate/n-hexane 2:1).

Yield: 1.5 g (5.1 mmol; 45%)

Example 1a'

Synthesis of (E)-But-2-enedioic acid 2-[2-ethanesulfinyl-ethyl)-methyl-amino]-ethyl ester methyl ester

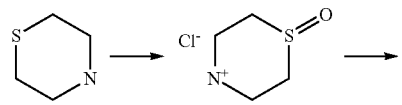

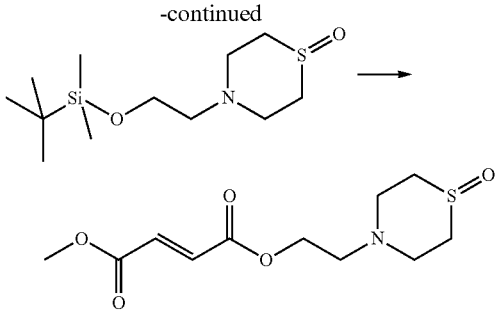

Thiomorpholine (10 g; 96.9 mmol) was dissolved in dry dichloromethane (350 mL), cooled to 0° C. and Ditert-butyl-dicarbonate (23.3 g; 107 mmol) dissolved in dichloromethane (100 mL) was added drop wise via dropping funnel (15 min). After complete addition the mixture was allowed to warm to room temperature and stirring was continued for 18 h.

The clear solution was concentrated under reduced pressure to a volume of 100 mL and washed with brine (50 mL), aqueous HCl (1N; 50 mL) and sat. sodium bicarbonate (100 mL). It was dried over sodium sulfate and concentrated under reduced pressure to achieve a white solid.

The white solid (22 g) was resolved in ethanol (150 mL), cooled to 0° C. and sodium periodate (27 g; 127 mmol) was added portion wise. The mixture was allowed to warm to room temperature and stirring was continued for 5 d.

The white suspension was concentrated under reduced pressure to half of its volume and afterwards diluted with water (300 mL). The mixture was extracted with dichloromethane (3×300 mL), the organic extracts washed with water (100 mL), dried over sodium sulfate and concentrated under reduced pressure. The crude product was suspended in n-hexane (150 mL) and treated with ultra sonic. The solids were filtered off, washed with n-hexane and dried under reduced pressure to yield 21 g of Boc-protected sulfoxide.

The crude material was diluted in dichloromethane (170 mL) and cooled to 0° C. after trifluoroacetic acid (50 mL) was added. The solution was allowed to warm to room temperature and stirring was continued for 18 h. The formed suspension was concentrated under reduced pressure to achieve a colorless solid. The TFA-salt was resolved in methanol (80 mL) and afterwards HCl (4N in dioxane; 50 mL) was added under stirring at room temperature. The formed white suspension was stirred for 1 h, filtered, washed with dichloromethane and dried under vacuum for 1 h to yield Thiomorpholine-1-oxide hydrochloride (11.3 g; 72.6 mmol; 75%) as colorless crystals.

Thiomorpholine-1-oxide hydrochloride (4 g; 25.7 mmol) was suspended in acetonitrile (127 mL) after Hünig's base (diisopropylethylamine; 13.1 mL; 77.8 mmol) was added and the resulting suspension sonicated until complete dissolution.

(2-Bromethoxy)-tert.-butyl-dimethylsilan (7.2 mL; 34.7 mmol) was added and the clear solution stirred at 80° C. over weekend (70 h).

The brown solution was concentrated under reduced pressure to a 5$^{th}$ of its volume and after ethyl acetate (150 mL) and water (100 mL) were added. The phases were separated, the aqueous layer extracted with ethyl acetate (150 mL) and all collected organic extracts washed with water (100 mL) and brine (70 mL), dried over sodium sulfate and concentrated under reduced pressure. The crude product was purified via silicagel chromatography (dichloromethane:methanol; 95:5) to yield 4-[2-(tert-Butyl-dimethyl-silanyloxy)-ethyl]-thiomorpholine-1-oxide (4.5 g; 16.2 mmol; 63%) as a yellowish oil.

4-[2-(tert-Butyl-dimethyl-silanyloxy)-ethyl]-thiomorpholine-1-oxide (1.07 g; 3.8 mmol) was dissolved in THF (10 mL) at room temperature and after tetrabutylammonium fluoride hydrate (1.82 g; 5.8 mmol) was added. The solution was stirred for 4 h at room temperature and afterwards concentrated under reduced pressure to yield the crude alcohol as a yellow oil.

Monomethyl fumarate (MMF) (0.5 g; 3.8 mmol) was suspended in dry dichloromethane (10 mL) at 0° C. and N-ethyl-N'-(3-methylaminopropyl)carbodiimide hydrochloride (0.81 g; 4.2 mmol) was added. The mixture was stirred for 2 min and crude alcohol dissolved in dichloromethane (2.5 mL) was added at 0° C. followed by DMAP (50 mg). The mixture was allowed to warm to room temperature and stirring was continued overnight. The brown mixture was diluted with additional dichloromethane (60 mL), washed twice with water (2×40 mL), dried over Na2SO4 and concentrated under reduced pressure. The crude product was purified via silicagel chromatography (ethyl acetate+5% trietylamine) to obtain (E)-But-2-enedioic acid methyl ester 2-(1-oxo-1lambda*4*-thiomorpholin-4-yl)-ethyl ester (290 mg; 11 mmol; 27.4%) as a colorless solid.

Example 1b

Synthesis of (E)-But-2-enedioic acid methyl ester 2-(4-methyl-piperazin-1-yl) ethyl dihydrochloride

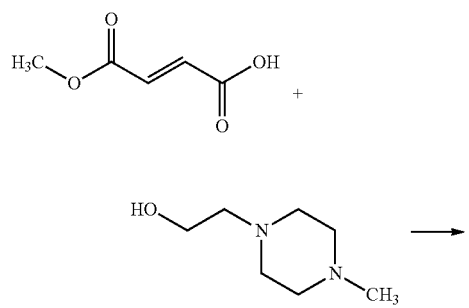

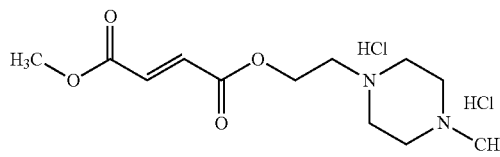

To a stirred suspension of monomethyl fumarate (1 eq.) in dry dichloromethane were added successively N-ethyl-N'-(3-methylaminopropyl)carbodiimide hydrochloride (1.1 eq.), 1-(2-hydroxyethyl) 4-methylpiperazine (0.98 eq.) and DMAP (0.1 eq.) at 0° C. The suspension was allowed to warm to room temperature (23° C.) and stirring was continued overnight (for 14 hours). The mixture was diluted with additional dichloromethane, washed with water and dried with sodium sulfate. The brown solution was treated with HCl (3M in butanol; 4 eq.) and the product was collected via filtration.

Example 1c

Synthesis of (E)-But-2-enedioic acid methyl ester 2-(4-isopropyl-piperazin-1-yl) ethyl dihydrochloride

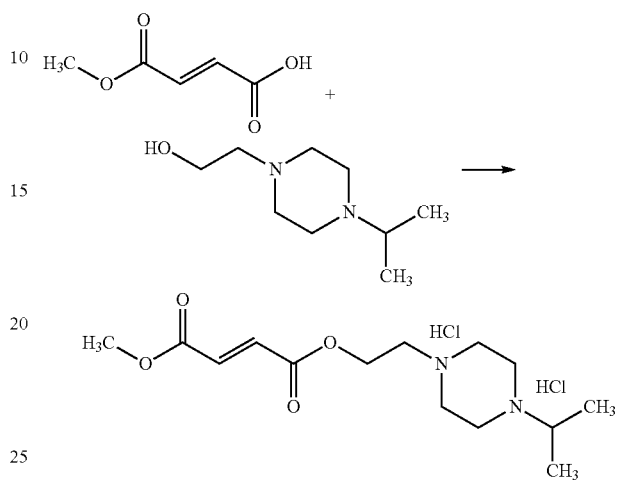

To a stirred suspension of monomethyl fumarate (1.5 g; 11.5 mmol) in dry dichloromethane (30 mL) were added successively N-ethyl-N'-(3-methylaminopropyl)carbodiimide hydrochloride (2.4 g; 12.7 mmol), 1-(2-hydroxyethyl)4-isopropylpiperazine (1.8 g; 10.4 mmol) and DMAP (140 mg; 1.2 mmol) at 0° C. The suspension was allowed to warm to room temperature (23° C.) and stirring was continued overnight (for 14 hours). The mixture was diluted with additional dichloromethane (50 mL), washed with water (2×70 mL) and dried with sodium sulfate. The crude product was subjected to a short silicagel chromatography (eluent: ethyl acetate) in order to partition off polar impurities. The remaining yellow residue was dissolved in dichloromethane (25 mL) and treated with HCl (3M in butanol; 10 mL) and the product was collected via filtration.

Yield: 814 mg (2.3 mmol; 20%)

Example 2

Synthesis of tris-[2-(E)-3-methoxycarbonylacryloyloxy)-ethyl]amine hydrochloride

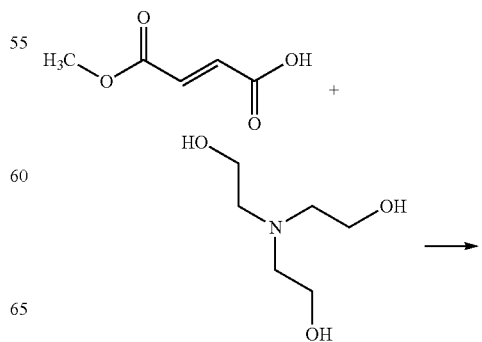

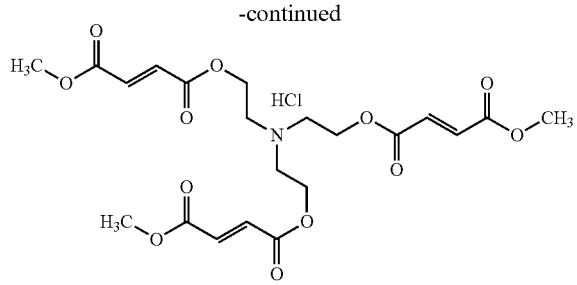

To a stirred suspension of monomethyl fumarate (4.6 g; 35.2 mmol) in dry dichloromethane (100 mL) were added successively N-ethyl-N'-(3-methylaminopropyl)carbodiimide hydrochloride (6.7 g; 35.2 mmol), tris-(2-hydroxyethyl)amine) (1.5 g; 10.1 mmol) and DMAP (123 mg; 1 mmol) at 0° C. The suspension was allowed to warm to room temperature (23° C.) and stirring was continued overnight (for 14 hours). The mixture was diluted with additional dichloromethane (50 mL), washed with water (2×70 mL) and dried with sodium sulfate. The resulting crude product was purified via silicagel chromatography (eluent: methyl tert-butyl ether/n-hexane 1:1). The free amine was dissolved in a mixture of dry diethyl ether/dichloromethane (3:1; 20 mL) and after HCl (4M in dioxane; 3 mL) was added and the precipitated product collected via filtration.

Yield: 1.02 g (2.0 mmol; 20%)

Example 3

Synthesis of (E)-but-2-enedioic acid 2,3-bis-(€-3-methoxycarbonyl-acryloyloxy)-propyl ester methyl ester

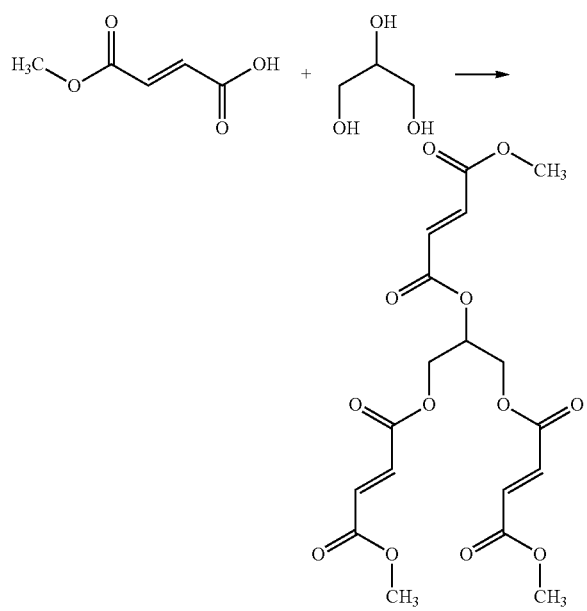

Glycerol (0.25 g, 2.71 mmol), monomethyl fumarate (1.4 g, 10.9 mmol), N-ethyl-N'-(3-methylaminopropyl)carbodiimide hydrochloride (2.081 g, 10.9 mmol) and 4-dimethylaminopyridine (DMAP; 0.02 g, 0.1 mmol) were dissolved in dry dichloromethane (20 ml). The reaction mixture was kept under continuous stirring at room temperature (23° C.) for 16 hours. The organic layer was washed three times with water (3×20 ml), the aqueous phase was washed with dichloromethane (40 ml) and the combined organic phases were dried over anhydrous sodium sulfate, filtered and concentrated in vacuo. The brownish/orange oily product was subjected to column chromatography (eluent: ethyl acetate/n-hexane 1:1) and the product was obtained as a colourless solid.

Example 4a

Synthesis of (E)-but-2-enedioic acid di-tert-butoxy-phosphoryloxymethyl ester methyl ester

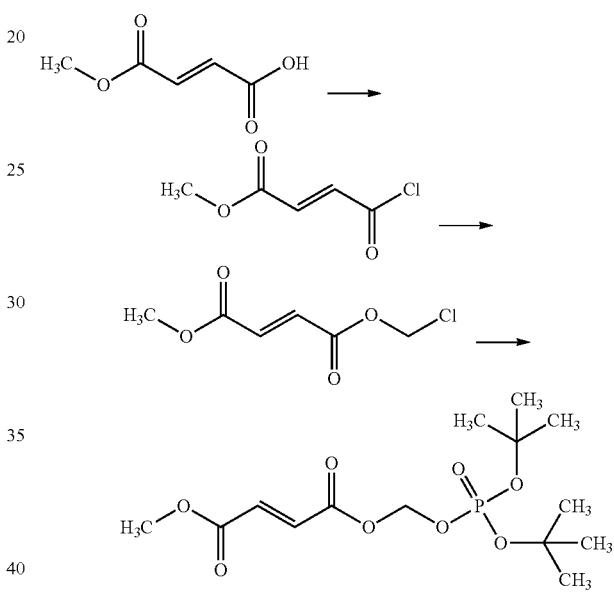

All glass equipment was dried at 110° C. overnight. Monomethyl fumarate (3.56 g) was suspended in 40 ml dichloromethane and placed in a 250 ml two-necked round-bottomed flask, equipped with an addition funnel, Vigreux distilling column and thermometer. The solution was heated to 40° C. Thionyl chloride (7.8 ml) was added within one hour through an addition funnel, so that gas formation could be observed. Dichloromethane was slowly distilled at 40° C. and the mixture was refluxed at 60-65° C. until gas formation stopped and no solids could be observed in the slightly yellow mixture. Excess thionyl chloride was distilled off under reduced pressure (bp.: 41° C./house vacuum) and methyl fumaroyl chloride was distilled at reduced pressure at about 32° C./oil pump. Yield: 1.61 g (39.7%) mp.: 12-13° C.

Under $N_2$ atmosphere, formaldehyde (22 mmol) was added dropwise to a stirred mixture of methyl fumaroyl chloride ((E)-3-chlorocarbonyl-acrylic acid methyl ester) (20 mmol) and catalytic amounts of $ZnCl_2$ at −20° C. After the addition of the acetaldehyde, the mixture was stirred for another hour at −20° C. Upon completion, the crude material was dissolved in petroleum ether, and eluted through a silica column (silica gel 60H, 6×8 cm) under suction. The eluted solution was filtered, evaporated, and the product, chloromethyl methyl fumarate, was isolated by vacuum distillation.

Under N₂-atmosphere, triethylamine (25 mmol) was added dropwise to a solution of di tert-butyl phosphate (20 mmol) and chloromethyl methyl fumarate (20 mmol) in dry DMF (10 mL). The reaction mixture was heated to 70° C. for 4 h and then the precipitate was filtered and washed with ethyl acetate. The filtrate was partitioned between water and ethyl acetate and the aqueous phase was washed with ethyl acetate. The combined organic phase was washed with water, 5% aqueous NaHCO₃-solution and with brine. After being dried over magnesium sulfate the organic solvent was evaporated to yield the crude product.

Example 4a'

Synthesis of (E)-but-2-enedioic acid di-tert-butoxy-phosphoryloxymethyl ester methyl ester

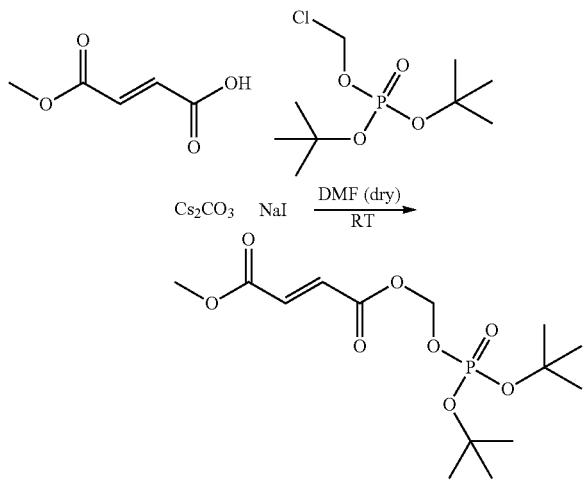

The educts were suspended in dimethylformamide and stirred for 12 hours at room temperature (23° C.). The mixture was concentrated and extracted with methyl tert-butyl ether and phosphate buffer. The solvent was removed and the crude product was purified by HPLC.

Preparative HPLC: 75 MeOH, Kromasil 100 A 10µ, 250×50 mm

Analytic HPLC: 75 MeOH, Kromasil 100 A 10µ, 250×4 mm

Alternatiev NP HPLC Prep/Analy:

Kromasil NP 60 A 10µ, 50 DCM 50 CAN

Yield: 47%

Example 4b

Synthesis of (E)-but-2-enedioic acid methyl ester 1-phosphonooxy-ethyl ester

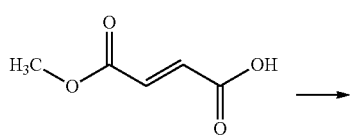

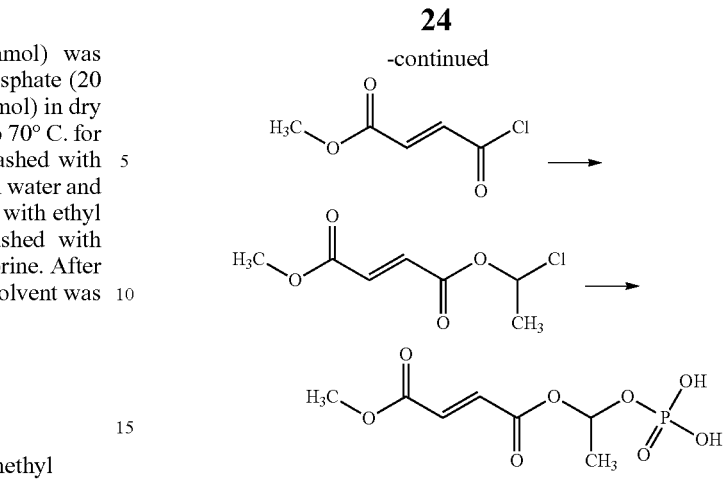

All glass equipment was dried at 110° C. overnight. Monomethyl fumarate (3.56 g) was suspended in 40 ml dichloromethane and placed in a 250 ml two-necked round-bottomed flask, equipped with an addition funnel, Vigreux distilling column and thermometer. The solution was heated to 40° C. Thionyl chloride (7.8 ml) was added within one hour through an addition funnel, so that gas formation could be observed. Dichloromethane was slowly distilled at 40° C. and the mixture was refluxed at 60-65° C. until gas formation stopped and no solids could be observed in the slightly yellow mixture. Excess thionyl chloride was distilled off under reduced pressure (bp.: 41° C./house vacuum) and methyl fumaroyl chloride was distilled at reduced pressure at about 32° C./oil pump. Yield: 1.61 g (39.7%) mp.: 12-13° C.

Under N₂ atmosphere, ice-cold acetaldehyde (22 mmol) was added dropwise to a stirred mixture of methyl fumaroyl chloride ((E)-3-chlorocarbonyl-acrylic acid methyl ester) (20 mmol) and catalytic amounts of ZnCl₂ at −20° C. After the addition of the acetaldehyde, the mixture was stirred for another hour at −20° C. Upon completion, the crude material was dissolved in petroleum ether, and eluted through a silica column (silica gel 60H, 6×8 cm) under suction. The eluted solution was filtered, evaporated, and the product, 1-chloroethyl methyl fumarate, was isolated by vacuum distillation.

Under N₂-atmosphere, triethylamine (25 mmol) was added dropwise to a solution of diethyl phosphate (20 mmol) and 1-chloroethyl methyl fumarate (20 mmol) in dry DMF (10 ml). The reaction mixture was heated to 70° C. for 4 h and then the precipitate was filtered and washed with ethyl acetate. The filtrate was partitioned between water and ethyl acetate and the aqueous phase was washed with ethyl acetate. The combined organic phase was washed with water, 5% aqueous NaHCO₃-solution and with brine. After having been dried over magnesium sulfate the organic solvent was evaporated to yield oily product, 1-(diethoxy-phosphoryloxy)ethyl methyl fumarate. A mixture of 6 ml acetic acid and 6 ml water was heated to 70° C. and a solution of the obtained 1-(diethoxyphosphoryloxy)ethyl methyl fumarate (10 mmol) in 10 mL methyl tert-butyl ether was added. After stirring the mixture for 2 hours the methyl tert-butyl ether was evaporated under reduced pressure (300 mbar). The remaining suspension was cooled to 10° C. and the precipitate was filtered off, washed with cold acetone and dried overnight to obtain the product.

Alternative Synthesis:

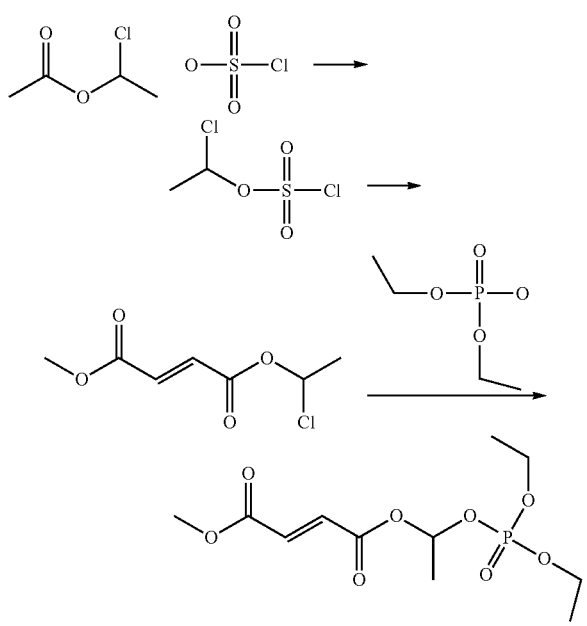

To Acetic acid 1-chloro-ethyl ester (54 g) was added chloro sulfuric acid (47 g) dropwise at 0° C. under stirring. The evolving HCl gas was removed by a constant flow of argon. The reaction mixture was slowly warmed to room temperature and stirred for 1 hour at this temperature. The reaction mixture was evaporated over night and the product was distilled afterwards at up to 90° C. to yield 30 g of the product as colorless oil (44%).

Monomethyl fumarate, sodium hydrogencarbonate (5 eq.), and tetrabutylammoniumsulfate (0.1 eq.) were suspended in 126 ml H$_2$O and 95 ml dichloromethane. Chloro sulfuric acid 1-chloro-ethyl ester (1.2 eq.) was added dropwise under vigorous stirring, stirring was continued overnight. After extraction with TBME the crude product was purified by HPLC (99.5% dichloromethane, 0.5% acetonitrile; Kromasil NP, 250×50 mm, 60 A 100 to obtain the pure product in 46% yield.

Diethyl phosphate (1 eq.), triethylamine (1.7 eq.), sodium iodide (0.01 eq.) and (E)-But-2-enedioic acid 1-chloro-ethyl ester methyl ester were suspended in acetonitrile. The reaction mixture was stirred for 2 days at 55° C. The solvent was evaporated and the crude product was purified by HPLC (98.75% dichloromethane, 1.25% methanol; Kromasil NP, 250×50, 60 A 100 to yield the product in 71% yield.

Example 5a

Synthesis of (E)-but-2-enedioic acid 2-((S)-2-amino-3-methyl-butyrryloxy)-ethyl ester methyl ester hydrochloride

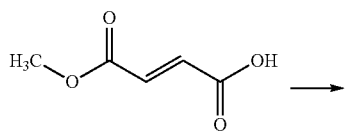

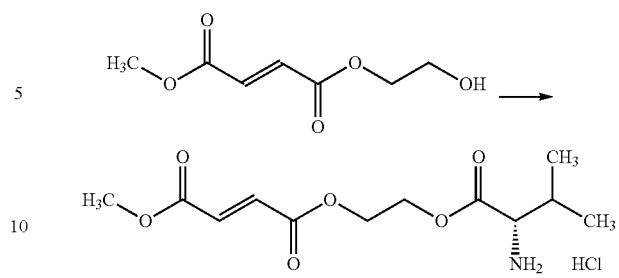

Monomethyl fumarate, ethylenglycol (5 eq.), EDC (2 eq.) and DMAP (0.01 eq.) were dissolved in acetonitrile. The reaction mixture was stirred for 4 hours. The product was extracted with ethylacetate/phosphate buffer pH 7.0. The crude product was purified by HPLC to obtain the product in a yield of 35%.

To (E)-But-2-enedioic acid 2-hydroxy-ethyl ester methyl ester, EDC (3 eq.), DMAP (0.01 eq.) and Boc-protected Valin was added acetonitrile. The reaction mixture was stirred for 12 hours at room temperature. The product was extracted with ethylacetate/phosphate buffer pH 7.0. The crude product was purified by HPLC to yield the product in a yield of 85%.

440 mg of (E)-But-2-enedioic acid 2-((S)-2-tert-butoxycarbonylamino-3-methyl-butyryloxy)-ethyl ester methyl ester was dissolved in acetic acid:chloroform 70:30. The reaction mixture was stirred for 4 days. The solvent was evaporated and the acetate salt was purified via HPLC ((Kromasil, 10μ, 100 A; 50% methanol, 0.1% trifluoracetic acid). The obtained trifluoracetate was dissolved in 0.1 N HCl and was evaporated to yield the hydrochloride in a yield of >95%.

Alternative Synthesis for (E)-but-2-enedioic acid 2-((S)-2-amino-3-methyl-butyrryloxy)-ethyl ester methyl ester

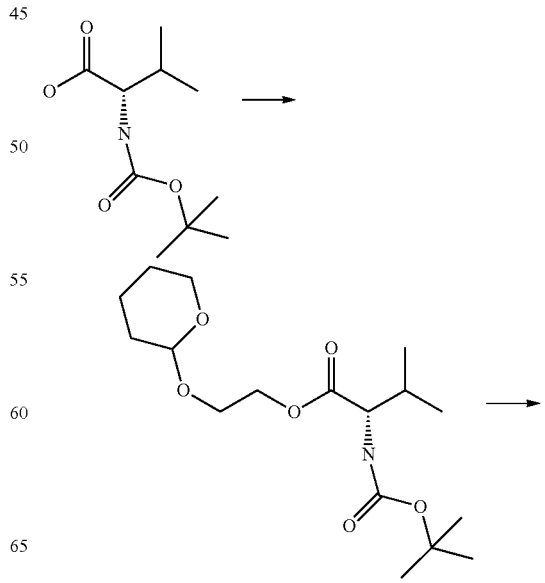

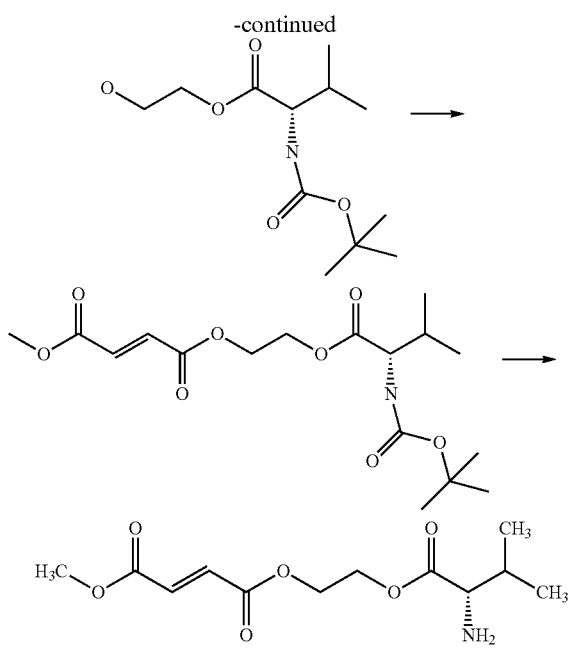

t-BOC-L-valine (2 g) was dissolved in dry dichloromethane (50 ml). DMAP (0.19 g) and THP-ethylene glycol (5.71 ml) was added under nitrogen. EDC (2.62 g) was added at room temperature and the reaction was stirred for 16 h at room temperature. Water (80 ml) was added to the reaction mixture, the organic layer was separated and evaporated at 40° C. The remaining residue was purified by column chromatography (diethylether/n-hexane (1/2 v/v) (visualizing of product on TLC was performed with KMnO$_4$ solution) to yield the product in 22% yield.

(S)-2-tert-Butoxycarbonylamino-3-methyl-butyric acid 2-(tetrahydro-pyran-2-yloxy)-ethyl ester (542 mg) and methanol (6 ml) were charged into 50 ml RBF. p-toluene sulfonic acid (31 mg) was added and the resulting mixture stirred at RT under argon for 1 h 15. Conversion was controlled by HPLC. The mixture was concentrated under reduced pressure. The residue was taken up with 50 ml dichloromethane and 25 ml saturated sodium bicarbonate solution. After decantation, the organic phase was dried over sodium sulphate and concentrated under reduced pressure yielding product as colourless oil (394 mg).

Under argon atmosphere, 454 mg (1.7 mmol) (S)-2-tert-Butoxycarbonylamino-3-methyl-butyric acid 2-hydroxyethyl ester was dissolved in 6 ml dichloromethane. After addition of 271 mg (2.1 mmol) monomethylfumarate and 11 mg (0.1 mmol) DMAP, the flask was placed in an ice bath. 433 mg EDC, dissolved in 3 ml dichloromethane was added dropwise within 5 min, the ice bath was removed and the mixture was stirred for 16 h at RT. The reaction mixture was diluted with 30 ml dichloromethane and the reaction was quenched by addition of 20 ml water. The organic phase was removed, washed with 20 ml water and 20 ml saturated sodium bicarbonate and dried over sodium sulfate. The solvent was removed in vacuum and the product, (E)-But-2-enedioic acid 2-((S)-2-tert-butoxycarbonylamino-3-methyl-butyryloxy)-ethyl ester methyl ester, was purified by flash chromatography (silica gel; solvent: 250 mL dichloromethane/methanol (99/1 with 0.25% triethylamine) followed by 200 mL dichloromethane/methanol (98/2 with 0.25% triethylamine).

Yield: 282 mg (43.5%)
Chemical purity (HPLC, λ=200 nm): 98.7%

Under argon atmosphere, 280 mg (0.7 mmol) (E)-But-2-enedioic acid 2-((S)-2-tert-butoxycarbonylamino-3-methyl-butyryloxy)-ethyl ester methyl ester was dissolved in 5 ml dichloromethane and the flask was placed in an ice bath. While stirring, 0.57 mL trifluoroacetic acid was added dropwise. After completion, the ice bath was removed and the mixture was stirred for 16 h at room temperature. The flask was again placed into an ice bath, 10 mL saturated sodium bicarbonate were added, the organic phase was separated and again washed with 10 mL saturated sodium bicarbonate. The solvent was removed and the residue dissolved in 30 mL ethyl acetate, washed with 15 mL saturated sodium bicarbonate and 15 mL brine and dried over sodium sulfate. After removal of the solvent, the product was obtained as a yellowish oil.

Yield: 185 mg (90.3%)
Chemical purity (HPLC, λ=200 nm): 93.3%

The synthesis of the HCl salt of the corresponding compound ((E)-but-2-enedioic acid 2-((S)-2-amino-3-methyl-butyrryloxy)-ethyl ester methyl ester hydrochloride) can be performed as described above.

Example 5b

Synthesis of (E)-but-2-enedioic acid 2-(2-amino-3-phenylpropanoyloxy)-ethyl ester methyl ester

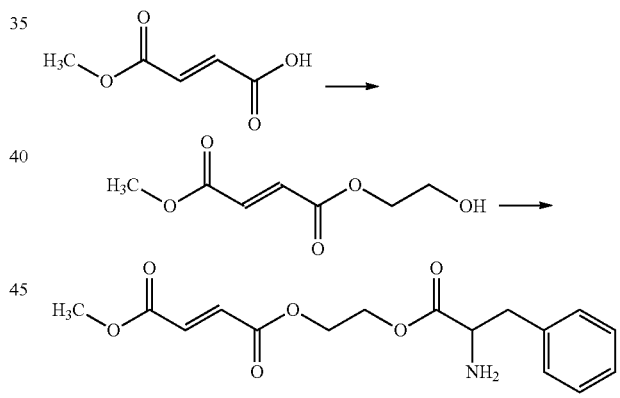

To a stirred solution of oxirane (1 eq.) in anhydrous acetonitrile, monomethyl fumarate (1 eq.) and a catalytic amount of tert.butyl ammonium bromide (0.03 eq.) were added. The resulting solution was then refluxed overnight. When all starting material had been used up the solvent was evaporated and the reaction mixture was dissolved in water and then extracted with chloroform and dried over magnesium sulfate. After filtration the solution was evaporated under reduced pressure to give the product, 2-hydroxyethyl methyl fumarate (but-2-enedioic acid 2-hydroxyethyl ester methyl ester).

2-Hydroxyethyl methyl fumarate (but-2-enedioic acid 2-hydroxyethyl, Boc-protected phenylalanine (353 mg, 1.1 eq.), DMAP (1.1 eq.) and N-ethyl-N'-(3-methylaminopropyl)carbodiimide hydrochloride (1.1 eq.) were mixed together and stirred in anhydrous dimethylformamide for 5 hours. After completion of the reaction, DMF was evaporated under reduced pressure and the residue purified using flash column chromatography. The obtained Boc-protected compound was solved in dichloromethane and trifluoroacetic acid was added dropwise at 0° C. The reaction mixture was allowed to warm to 23° C. and after completion of the reaction the obtained trifluoracetic acid salt was neutralized with aqueous $Na_2CO_3$-solution. Further, dichloromethane was added and the organic layer was separated. The aqueous layer was further extracted three times with ethyl acetate. The combined organic layers were dried over magnesium sulfate and the solvent was evaporated under reduced pressure to yield the product in the form of its free base.

Example 6

Synthesis of (E)-but-2-enedioic acid methyl ester5-methyl-2-oxo-[1,3]dioxol-4-yl methyl ester

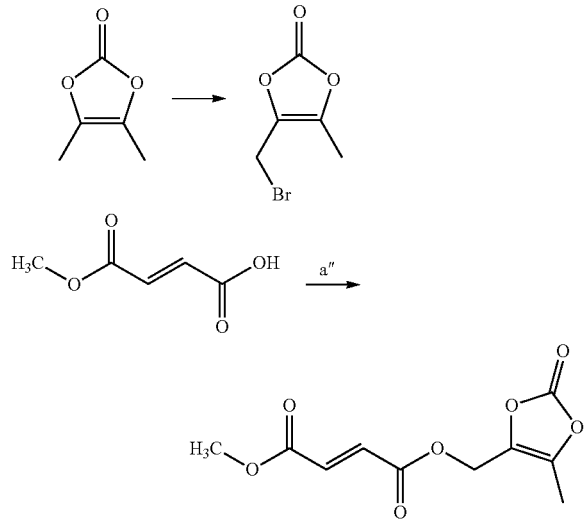

A mixture of 4,5-dimethyl-1,3-dioxol-2-one (6 g; 52.6 mmol), N-bromosuccinimide (NBS; 9.36 g; 52.6 mmol) and benzoyl peroxide (0.36 g; 1.5 mmol) in $CCl_4$ 80 mL was stirred at 77° C. for 1 h. After cooling to 23° C. the solution was treated with aqueous $NaHCO_3$-solution (20 mL) and the phases were separated. The aqueous phase was extracted three times with dichloromethane (3×40 mL), the combined organic phases were dried over sodium sulfate and all solvents evaporated under reduced pressure to obtain crude 4-(bromomethyl)-5-methyl-1,3-dioxol-2-one.

Under $N_2$ atmosphere, a mixture of monomethyl fumarate (2 g; 15.4 mmol), 4-(bromomethyl)-5-methyl-1,3-dioxol-2-one (7 g), $K_2CO_3$ (2.1 g; 15.4 mmol) and sodium iodide (2.3 g; 15.4 mmol) in anhydrous DMF (8 mL) was stirred for 15 h at 23° C. The mixture was quenched with water (25 mL) and extracted with ethyl acetate (2×50 mL). The organic phase was washed with water (30 mL), dried over sodium sulfate and concentrated under reduced pressure. The crude product was purified via silicagel chromatography (eluent: ethyl acetate/n-hexane 3:1).

Yield: 1.85 g (7.6 mmol; 50%)

Example 7

Investigation and Comparison of the Kinetic of MMF-Release of the Different Compounds of the Present Invention and DMF During Incubation in Intestinal Fluid from the Minipig 1. Materials
1.1. Test Compounds
Compounds of the present invention were synthesized as described above.
1.2. Intestinal Fluid
Intestinal fluid samples were prepared at CiToxLAB Scantox A/S. The samples were taken from 1 female Göttingen SPF minipig from CiToxLAB Scantox A/S standard stock, originally obtained from Ellegaard Göttingen Minipigs A/S, DK-4261 Dalmose, Denmark. The minipig was 10 months old and the body weight was 21 kg. The minipig was identified by an individual number tagged to the pinna of one ear (animal number is documented in the raw data).

The minipig was fasted for approximately 28 hours before sampling of intestinal fluid. On the day of sampling, the minipig was weighed and anaesthetised by an intramuscular injection in the neck or in the left hind leg (about 0.3 ml per kg body weight) of a mixture of Zoletil 50 Vet., Virbac, France (125 mg tiletamine and 125 mg zolazepam), Rompun Vet., Bayer, Germany (20 mg xylazine/ml, 6.5 ml), Ketaminol Vet., Veterinaria AG, Switzerland (100 mg ketamine/ml, 1.5 ml) and Methadon DAK, Nycomed Danmark, Denmark (10 mg methadon/ml, 2.5 ml).

Intestinal fluid was obtained by flushing one jejunal segment, measuring 30.2 cm, with saline. Intestinal fluid together with saline used for flushing was placed in centrifuge tubes. All samples were frozen at −70° C. and shipped on dry ice to the Sponsor for further use.

2. Analytical Methods
2.1. Quantification of MMF by LC-MS
2.1.1. Analytical Instrument
Instrument: Acquity UPLC system coupled with a TQ detector (triple quadruple mass spectrometer)
UPLC Method:
Column: Phenomenex Kinetex C18, 100 A, 2.6 µm (150×4.6 mm)
flow: 0.4 ml/min
split: appr. 100 µl/min to MS
temperature 30° C.
solvent system (isocratic):
Solvent A 25% water with 0.1% acetic acid
Solvent B 75% methanol with 0.1% acetic acid
stoptime: 6 min
autosampler temperature: 8° C.
injection volume: 4 µl
retention time: MMF: 4.3 min
MEF: 4.7 min
Mass Spectrometry
software: Masslynx 4.1
detection mode: electrospray/negative ions (ESP−)
capillary voltage: 2.3 kV
source temperature: 100° C.
desolvation temperature: 450° C.
cone voltage: 18 V
desolvation gas: $N_2$, 650 L/h
cone gas: $N_2$, 20 L/h
collision gas: argon, appr. $3.3*10^{-3}$ mbar
collision energy: 11 eV MRM [m/z]: 128.94>85.03 Monomethylfumarate dwell:200 msec
142.99>99.06 Monoethylfumarate (ISTD) dwell:200 msec 2.1.2. Stock and Calibration Solutions Stock (SS), working (WS) and calibration solutions of the analyte monomethyl fumarate (MMF) and the internal standard (ISTD) monoethyl fumarate (MEF) were prepared as described below.

$SS_{MMF}$: In a 10 ml volumetric flask, 6.5 mg MMF (Batch: MKRJ0642V/Aldrich) were dissolved in methanol and made up to volume (c=650 µg/ml)

$SS_{ISTD}$: In a 100 ml volumetric flask, 10 mg MEF (Batch: STBC5219V/Aldrich) were dissolved in methanol and made up to volume (c=100 µg/ml)

$WS_{ISTD}$: 100 µl SSISTD were transferred into a 10 ml volumetric flask and made up to volume with acetonitrile (c=1,000 ng/ml);

Calibration solutions were prepared by serial dilution of $SS_{MMF}$; diluted small intestinal fluid (diluted by 1/20 v/v with 50 mM $KH_2PO_4$, pH 6.8; (dil IF) was used as matrix. The dilution scheme is given below:

| calibration solution | Preparation | | Concentration | |
|---|---|---|---|---|
| | | | [ng/ml] | [µM] |
| cal6500 | 8 µl $SS_{MMF}$ | +792 µl dil IF | 6,500 | 50 |
| cal3250 | 50 µl cal6500 | +50 µl dil IF | 3250 | 25 |
| cal650 | 20 µl cal6500 | +180 µl dil IF | 650 | 5.0 |
| cal 325 | 50 µl cal650 | +50 µl dil IF | 325 | 2.5 |
| cal65 | 10 µl cal650 | +90 µl dil IF | 65 | 0.5 |

2.1.3. Sample Preparation

50 µl sample (calibration solution or sample of an incubation experiment with MMF prodrugs) was mixed with 50 µl $WS_{ISTD}$, 20 µl formic acid and 100 µl acetonitrile. This mixture was vortexed for 15 sec and centrifuged (13,000 rpm, 3 min). Thereafter, 4 µl of the supernatant were subjected to LC-MS analysis.

2.2. Incubation Experiments with DMF (Reference) and Compounds of the Invention 2.2.1. Stock Solutions Stock solutions were prepared in DMSO or in DMSO with 10% (v/v) with water. Concentrations in stock solutions were 5.00, 2.50 and 1.67 mmol for compounds with one, two and three molar MMF equivalents.

| Compound | MW | Sample weight [mg] | dissolved in | Concentration [mg/ml] | [mmol] |
|---|---|---|---|---|---|
| DMF | 144.13 | 7.21 | 10 ml DMSO | 0.721 | 5.00 |
| Example 1a | 291.33 | 7.28 | 5 ml DMSO | 1.456 | 5.00 |
| Example 1a' | 275.33 | 6.89 | 5 ml DMSO | 1.378 | 5.00 |
| Example 1b | 329.22 | 8.23 | 5 ml DMSO | 1.646 | 5.00 |
| Example 1c | 357.27 | 8.93 | 5 ml DMSO | 1.786 | 5.00 |
| Example 2 | 521.91 | 4.35 | 5 ml DMSO | 0.87 | 1.67 |
| Example 3 | 428.35 | 3.57 | 5 ml DMSO | 0.714 | 1.67 |
| Example 4a | 352.32 | 8.81 | 5 ml DMSO | 1.762 | 5.00 |
| Example 5a | 309.75 | 7.74 | 5 ml DMSO | 1.548 | 5.00 |
| Example 6 | 242.19 | 6.05 | 5 ml DMSO | 1.21 | 5.00 |

2.2.2. Incubation Experiment

In a HPLC glass vial, 8 µl of stock solution were mixed with 792 µl dil IF and the mixture was stirred (250 rpm) in a water bath (T=37° C.).

Immediately after mixing as well as at t=15 min, 30 min, 60 min, 90 min and 120 min, 50 µl were withdrawn and prepared for LC-MS analysis as described in chapter. 2.1.3.

Incubations were continued and in case the result of analysis of the 120 min indicated the presence of remaining intact MMF-prodrug, additional samples were taken (t=360 or 420 min and at 1,260 or 1,320 min) and analysed.

3. Results 3.1. Calibration of the Analytical Method

Each calibration solution was analysed two-fold. The second analysis was carried out approx. 18 h after storage of the sample in the autosampler, which was cooled to 8° C. The results demonstrate that the ratio of peak area remains essentially unchanged between the first and the second analysis.

The concentration/peak area ratio data pairs were subjected to regression analysis with 1/x weighting and the resulting calibration equation was used to quantify the MMF content in incubation samples.

| calibration standard | nominal concentration [ng/ml] | Analysis | area/ area(ISTD) | mean | RSD |
|---|---|---|---|---|---|
| cal6500 | 6,500 | $1^{st}$ analysis | 3.569 | 3.567 | 0.07 |
| | | $2^{nd}$ analysis | 3.564 | | |
| cal3250 | 3,250 | $1^{st}$ analysis | 1.710 | 1.681 | 1.73 |
| | | $2^{nd}$ analysis | 1.652 | | |
| cal650 | 650 | $1^{st}$ analysis | 0.348 | 0.347 | 0.29 |
| | | $2^{nd}$ analysis | 0.346 | | |
| cal325 | 325 | $1^{st}$ analysis | 0.174 | 0.169 | 2.96 |
| | | $2^{nd}$ analysis | 0.164 | | |
| cal65 | 65 | $1^{st}$ analysis | 0.036 | 0.035 | 2.86 |
| | | $2^{nd}$ analysis | 0.034 | | |
| cal0 | 0 | $1^{st}$ analysis | 0.000 | 0.000 | 0.00 |
| | | $2^{nd}$ analysis | 0.000 | | |

Figure 2:
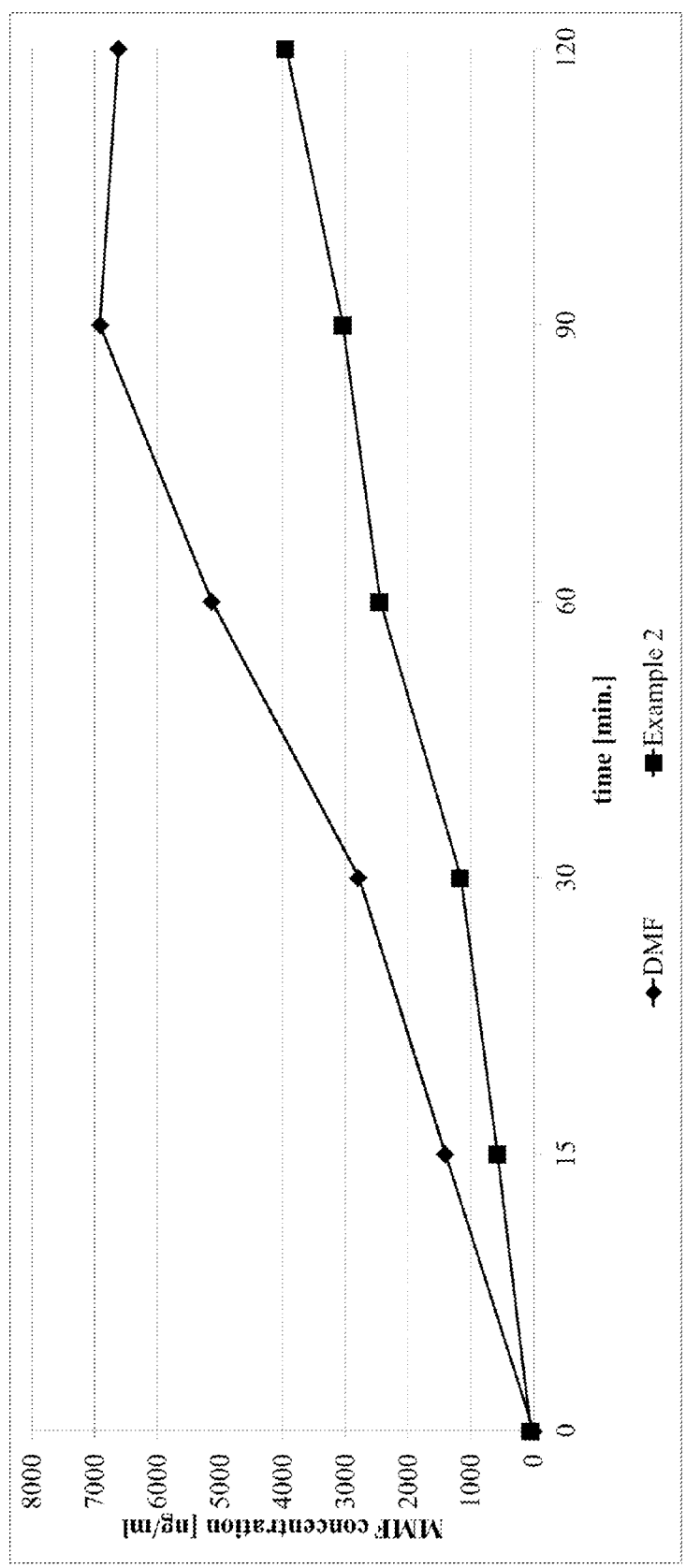
FIG. 2 depicts data of Example 2, showing significantly slower hydrolysis to MMF than DMF.
Figure 3:
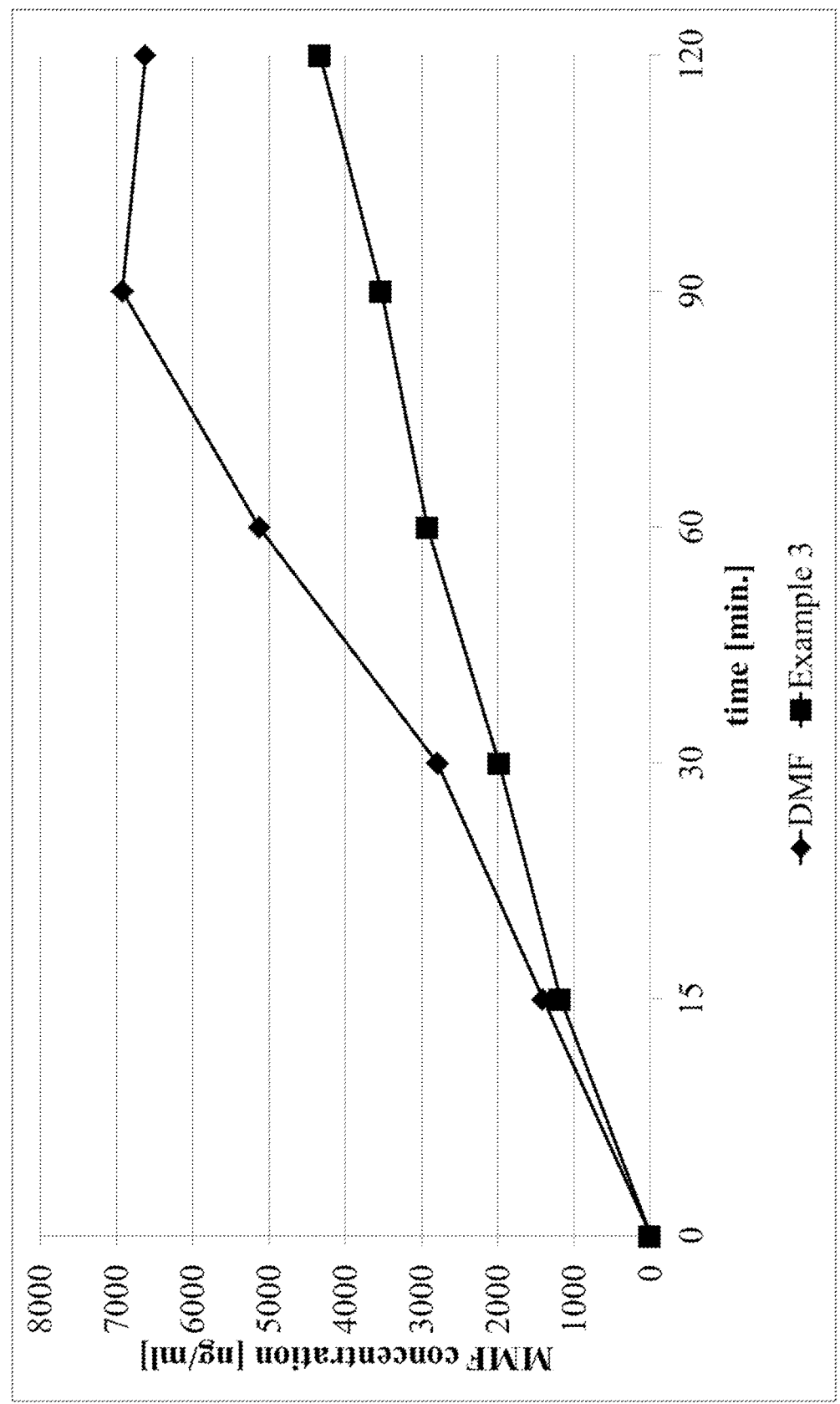
FIG. 3 depicts data of Example 3, showing significantly slower hydrolysis to MMF than DMF.
Figure 4:
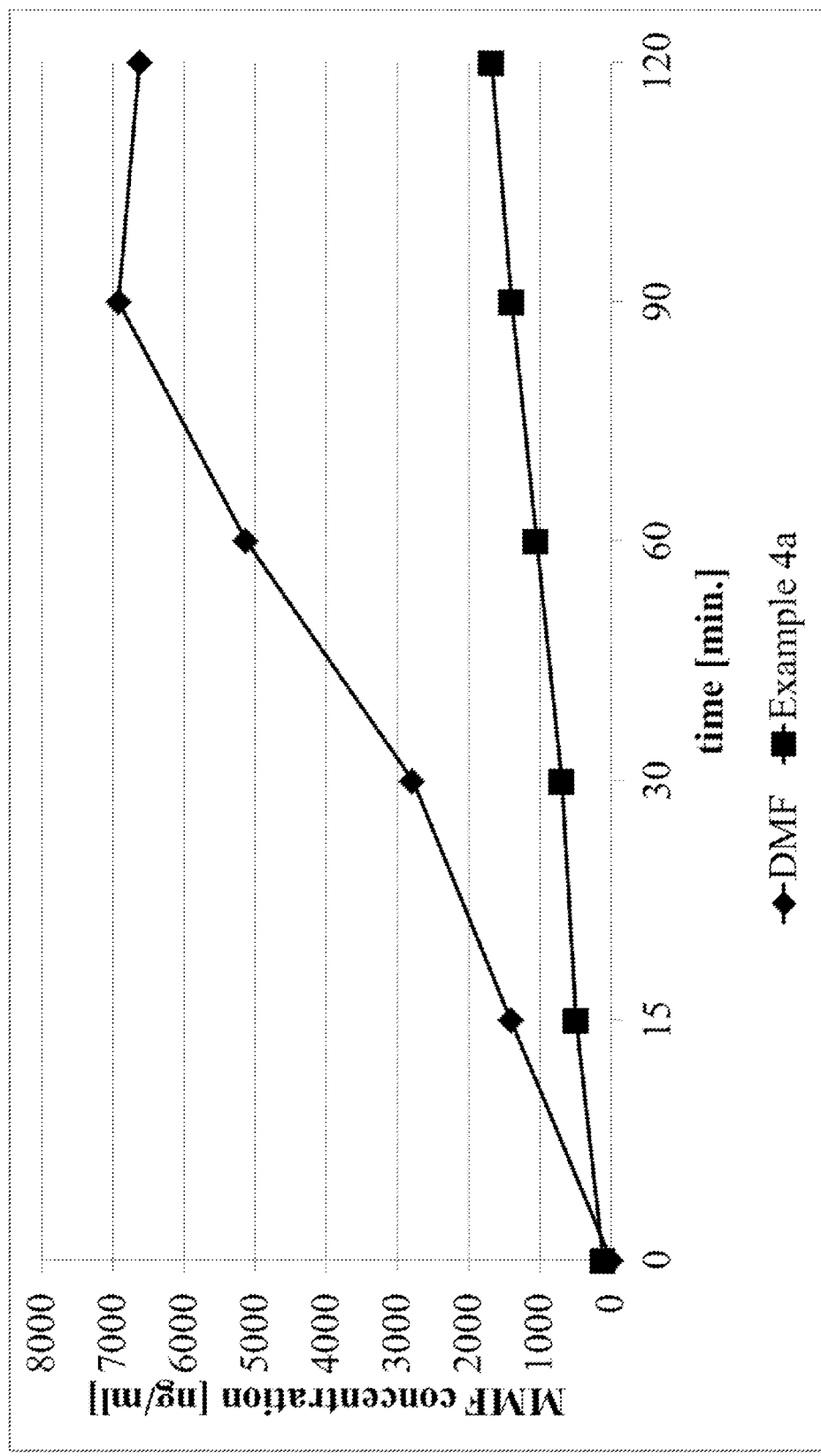
FIG. 4 depicts data of Example 4a, showing significantly slower hydrolysis to MMF than DMF.
Figure 5:
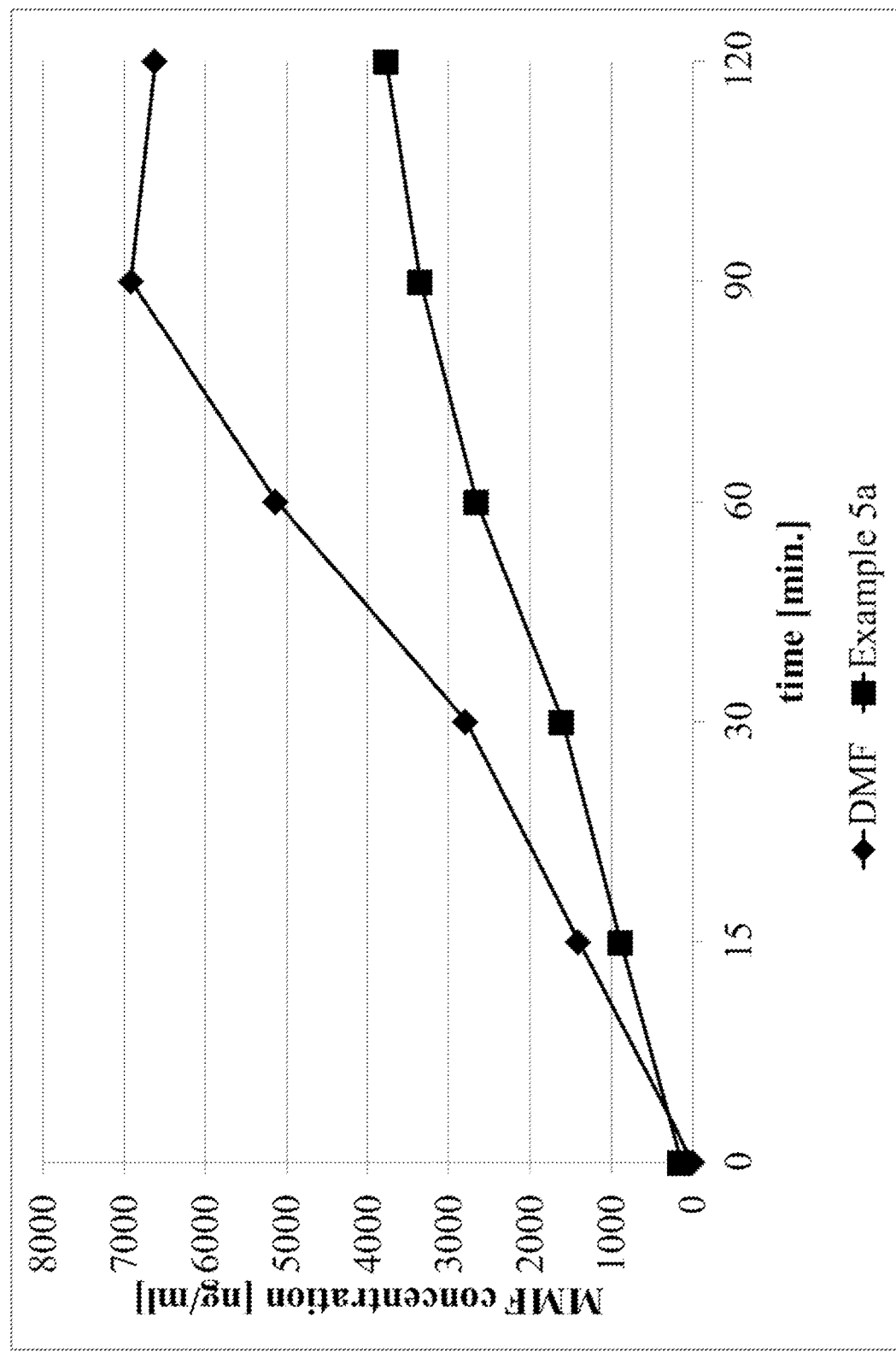
FIG. 5 depicts data of Examples 5a, showing significantly slower hydrolysis to MMF than DMF.
Figure 6:
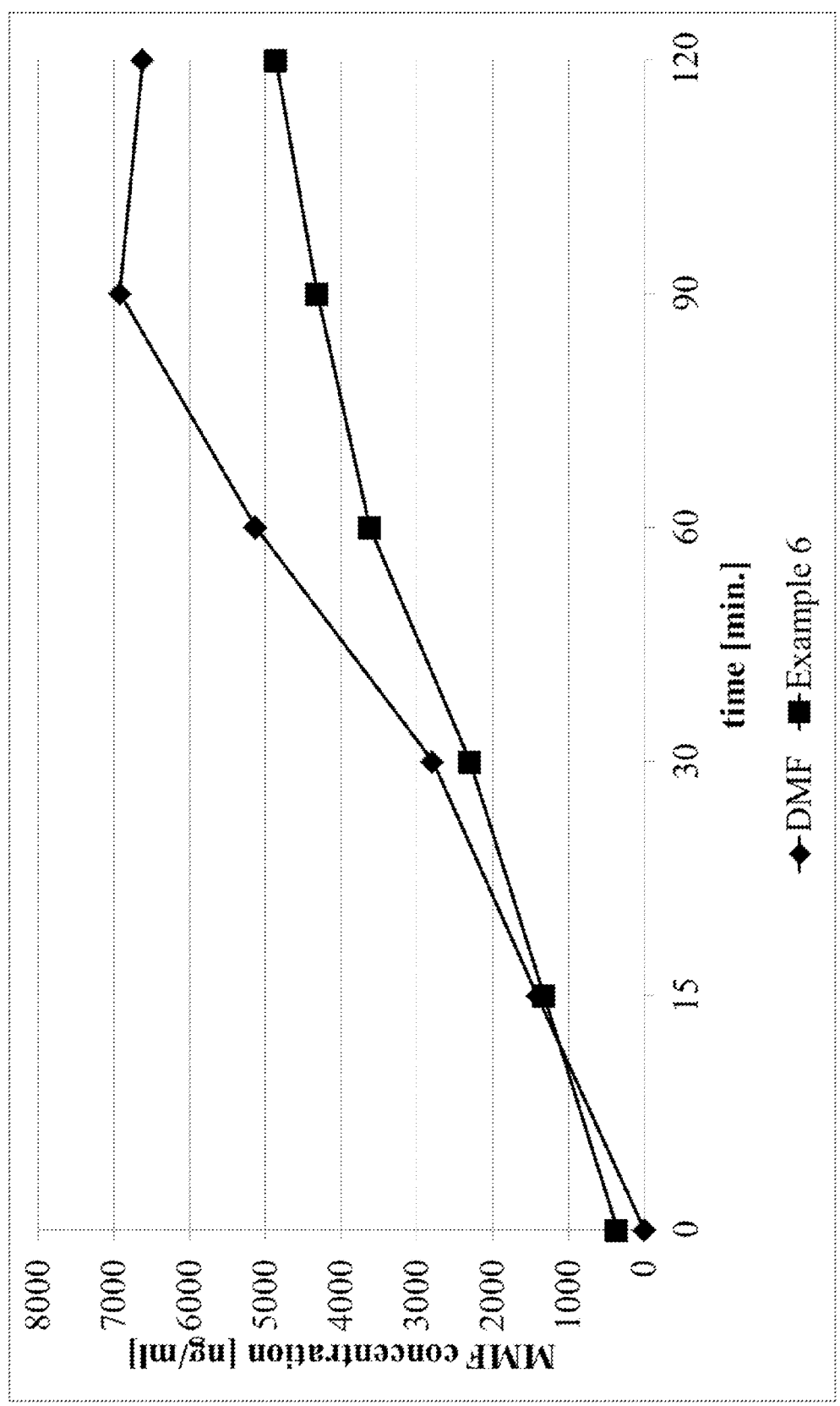
FIG. 6 depicts data of Example 6, showing significantly slower hydrolysis to MMF than DMF.

As can be seen from FIGS. 1 to 6 the inventive compounds according to Formulae (I) to (VI) show a desirable significantly slower hydrolysis to MMF than DMF.

The invention claimed is:

1. A compound according to any one of the following Formulae (I) to (VI) or mixtures thereof for use as a medicament:

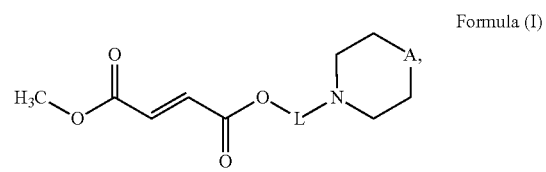

Formula (I)

wherein

L is an alkanediyl group with 1 to 6 carbon atoms, and

A is SO, $SO_2$ or $NR^1$, wherein $R^1$ is isopropyl or a cycloalkyl with 3, 5 or 6 carbon atoms.

2. The compound according to claim 1, wherein L is a linear alkanediyl group and A is $SO_2$.

3. The compound according to claim 2 represented by Formula (Ia)

Formula (Ia)

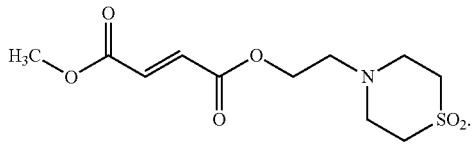

4. The compound according to claim 1, wherein L is a linear alkanediyl group and A is SO$_2$.

5. The compound according to claim 4 represented by Formula (Ia')

Formula (Ia')

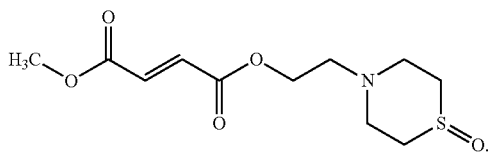

6. The compound according to claim 1, wherein L is a linear alkanediyl group and A is NR$^1$.

7. The compound according to claim 6 represented by Formula (Ic)

Formula (Ic)

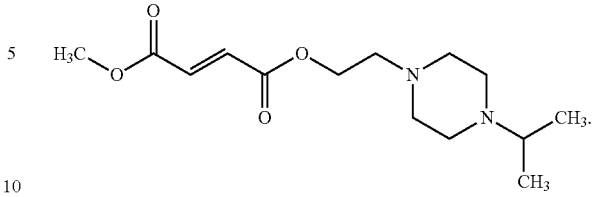

8. The compound according to claim 1 for the use in the treatment of systemic diseases, autoimmune diseases or inflammatory diseases, preferably for the use in the treatment of multiple sclerosis or psoriasis.

9. A pharmaceutical composition comprising a compound according to claim 1.

10. The pharmaceutical composition according to claim 9, comprising
 (i) 0.01 to 10 mmol of a compound according to and
 (ii) optionally pharmaceutical excipients.

11. The pharmaceutical composition according to claim 10, wherein the composition is a solid oral dosage form.

12. The pharmaceutical composition according to claim 11, wherein the in-vitro drug release after 2 hours is less than 10%, measured according to USP, Apparatus II, paddle, 0.1 N HCl, 37° C., 50 rpm.

* * * * *